US008859496B2

(12) United States Patent  
Ryu et al.

(10) Patent No.: US 8,859,496 B2  
(45) Date of Patent: Oct. 14, 2014

(54) PHARMACEUTICAL COMPOSITION USING CONNECTIVE-TISSUE GROWTH FACTOR

(75) Inventors: Sung Ho Ryu, Pohang-si (KR); Pann-Ghill Suh, Pohang-si (KR); Mi-Sook Lee, Pohang-si (KR); Wan-Uk Kim, Suwon-si (KR)

(73) Assignee: Postech Academy-Industry Foundation, Pohang (KR)

( * ) Notice: Subject to any disclaimer, the term of this patent is extended or adjusted under 35 U.S.C. 154(b) by 0 days.

(21) Appl. No.: 13/642,143

(22) PCT Filed: Feb. 21, 2011

(86) PCT No.: PCT/KR2011/001125
§ 371 (c)(1),
(2), (4) Date: Oct. 19, 2012

(87) PCT Pub. No.: WO2011/136469
PCT Pub. Date: Nov. 3, 2011

(65) Prior Publication Data
US 2013/0039918 A1 Feb. 14, 2013

Related U.S. Application Data

(60) Provisional application No. 61/328,686, filed on Apr. 28, 2010.

(30) Foreign Application Priority Data

Dec. 22, 2010 (KR) .................... 10-2010-0132775

(51) Int. Cl.
*A61K 38/18* (2006.01)

(52) U.S. Cl.
CPC .................................... *A61K 38/18* (2013.01)
USPC ................ 514/7.6; 514/13.3; 514/21.3

(58) Field of Classification Search
CPC ........................ A61K 38/18; C07K 14/475
See application file for complete search history.

(56) References Cited

U.S. PATENT DOCUMENTS

| 5,408,040 A * | 4/1995 | Grotendorst et al. ......... 530/399 |
| 2006/0034863 A1 | 2/2006 | Schall |
| 2006/0281668 A1 | 12/2006 | Parobok |
| 2009/0232773 A1 | 9/2009 | Kato |
| 2009/0325302 A1 | 12/2009 | Jaffa |

FOREIGN PATENT DOCUMENTS

| CN | 1334819 | 2/2002 |
| CN | 101160138 | 4/2008 |
| EP | 1600109 A1 | 11/2005 |
| JP | 11-507332 | 6/1999 |
| JP | 2002-532084 | 10/2002 |
| JP | 2008-525460 | 7/2008 |
| WO | 96/38172 | 12/1996 |
| WO | 00/35939 | 6/2000 |
| WO | 01/15729 | 3/2001 |
| WO | 03/053340 | 7/2003 |
| WO | 2006/069037 | 6/2006 |
| WO | 2007/066823 | 6/2007 |
| WO | 2010/027830 | 3/2010 |
| WO | 2010/027831 | 3/2010 |
| WO | 2010/042281 | 4/2010 |

OTHER PUBLICATIONS

Shimo et al., J. Biochem (Tokyo), 126:137-145, 1999.*
Inoki et al., FASEB J., 16:219-221, 2002.*
Feng Tian, et al., "Role of connective tissue growth factor on pulmonary artery remodeling in rats exposed to smoke", Chin J Tuberc Respir Dis, vol. 30, No. 12, pp. 921-925 (Dec. 2007).
Halleck, A., et al., "Cloning of human full open reading frames in Gateway (TM) system entry vector (pDONR201)", CAG46534, GenBank, (Oct. 16, 2008).
Rembert Koczulla, et al., "An angiogenic role for the human peptide antibiotic LL-37/hCAP-18", The Journal of Clinical Investigation, vol. 111, No. 11, pp. 1665-1672 (Jun. 2003).
Alexander M. Babic, et al., "Fisp12/Mouse Connective Tissue Growth Factor Mediates Endothellial Cell Adhesion and Migration through Integrin alphavbeta3, Promotes Endothelial Cell Survival, and Induces Angiogenesis In Vivo," Molecular and Celllular Biology, American Society for Microbiology, Washington, US, vol. 19, No. 4, pp. 2958-2966, (Apr. 1999).
Sanja Ivkovic, et al., "Connective tissue growth factor coordinates chondrogenesis and angiogenesis during skeletal development," Development, Company of Biologists, Cambridge, GB, vol. 130, pp. 2779-2791, (Jun. 2003).

* cited by examiner

*Primary Examiner* — Marianne P Allen
(74) *Attorney, Agent, or Firm* — Lexyoume IP Meister, PLLC

(57) ABSTRACT

This disclosure relates to an angiogenesis-related pharmaceutical composition using connective tissue growth factor, more particularly to a pharmaceutical composition for promoting angiogenesis containing the connective tissue growth factor or a pharmaceutical composition for inhibiting angiogenesis containing at least one selected from the group consisting of polypeptide, antibody and a compound binding to connective tissue growth factor. The fragment of connective tissue growth factor protein, which was found out in the present invention, is a binding region to FPRL1, effectively induces FPRL1-specific ERK phosphorylation, activates FPRL1 to increase intracellular $Ca^{2+}$ concentration, and finally, effectively induces angiogenesis, and thus, the fragment of connective tissue growth factor may be useful for a pharmaceutical composition for promoting angiogenesis, while polypeptide, antibody or a compound binding to the fragment of connective tissue growth factor protein may be useful for a pharmaceutical composition for inhibiting angiogenesis.

1 Claim, 22 Drawing Sheets

Fig. 4

MTAASMGPVRVAFVVLLALCSRPAVG
QNCSGPCRCPDEPAPRCPAGVSLVLD
GCGCCRVCAKQLGELCTERDPCDPH
KGLFCDFGSPANRKIGVCTAKDGAPCI
FGGTVYRSGESFQSSCKYQCTCLDGA
VGCMPLCSMDVRLPSPDCPFPRRVKL
PGKCCEEWVCDEPKDQTVVGPALAAY
RLEDTFGPDPTMIRANCLVQTTEWSA
CSKTCGMGISTRVTNDNASCRLEKQS
RLCMVRPCEADLEENIKKGKKCIRTPK
ISKPIKFELSGCTSMKTYRAKFCGVCT
DGRCCTPHRTTTLPVEFKCPDGEVMK
KNMMFIKTCACHYNCPGDNDIFESLYY
RKMYGDMA

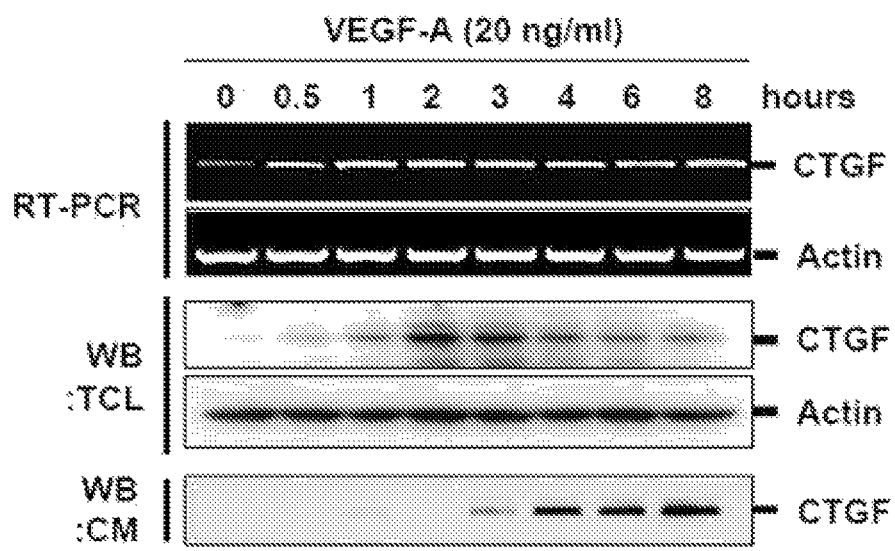

Fig. 5

```
                        SEQUENCE LISTING

<160> NUMBER OF SEQ ID NOS: 16

<210> SEQ ID NO 1
<211> LENGTH: 6
<212> TYPE: PRT
<213> ORGANISM: Artificial Sequence
<220> FEATURE:
<223> OTHER INFORMATION: Agonistic peptide, wherein the 6th amino acid
      is D-Met

<400> SEQUENCE: 1

Trp Lys Tyr Met Val Met
 1               5

<210> SEQ ID NO 2
<211> LENGTH: 6
<212> TYPE: PRT
<213> ORGANISM: Artificial Sequence
<220> FEATURE:
<223> OTHER INFORMATION: FPRL1 antagonist

<400> SEQUENCE: 2

Trp Arg Trp Trp Trp Trp
 1               5

<210> SEQ ID NO 3
<211> LENGTH: 19
<212> TYPE: RNA
<213> ORGANISM: Artificial Sequence
<220> FEATURE:
<223> OTHER INFORMATION: Sense strand of FPRL1 siRNA, wherein 'dTdT' is
      attached to 3' end

<400> SEQUENCE: 3
uucacaucgu gguggacau                                                  19

<210> SEQ ID NO 4
<211> LENGTH: 19
```

```
<212> TYPE: RNA
<213> ORGANISM: Artificial Sequence
<220> FEATURE:
<223> OTHER INFORMATION: Anti-sense strand of FPRL1 siRNA, wherein
      'dTdT' is attached to 3' end

<400> SEQUENCE: 4
auguccacca cgaugugaa                                                    19

<210> SEQ ID NO 5
<211> LENGTH: 38
<212> TYPE: PRT
<213> ORGANISM: Artificial Sequence
<220> FEATURE:
<223> OTHER INFORMATION: Amino acid sequence of linker region of CTGF

<400> SEQUENCE: 5

Trp Val Cys Asp Glu Pro Lys Asp Gln Thr Val Val Gly Pro Ala Leu
 1               5                  10                  15

Ala Ala Tyr Arg Leu Glu Asp Thr Phe Gly Pro Asp Pro Thr Met Ile
            20                  25                  30

Arg Ala Asn Cys Leu Val
        35

<210> SEQ ID NO 6
<211> LENGTH: 39
<212> TYPE: PRT
<213> ORGANISM: Artificial Sequence
<220> FEATURE:
<223> OTHER INFORMATION: Amino acid sequence of linker polypeptide
      comprising the linker region of SEQ ID NO: 5

<400> SEQUENCE: 6

Glu Trp Val Cys Asp Glu Pro Lys Asp Gln Thr Val Val Gly Pro Ala
 1               5                  10                  15

Leu Ala Ala Tyr Arg Leu Glu Asp Thr Phe Gly Pro Asp Pro Thr Met
            20                  25                  30

Ile Arg Ala Asn Cys Leu Val
        35

<210> SEQ ID NO 7
<211> LENGTH: 114
<212> TYPE: DNA
<213> ORGANISM: Artificial Sequence
<220> FEATURE:
<223> OTHER INFORMATION: Nucleotide sequence for the linker region of
      SEQ ID NO: 5

<400> SEQUENCE: 7
tgggtgtgtg acgagcccaa ggaccaaacc gtggttgggc ctgccctcgc ggcttaccga      60
ctggaagaca cgtttggccc agacccaact atgattagag ccaactgcct ggtc          114

<210> SEQ ID NO 8
<211> LENGTH: 117
<212> TYPE: DNA
<213> ORGANISM: Artificial Sequence
<220> FEATURE:
<223> OTHER INFORMATION: Nucleotide sequence for the linker polypeptide
      of SEQ ID NO: 6

<400> SEQUENCE: 8
gagtgggtgt gtgacgagcc caaggaccaa accgtggttg ggcctgccct cgcggcttac      60
cgactggaag acacgtttgg cccagaccca actatgatta gagccaactg cctggtc       117
```

<210> SEQ ID NO 9
<211> LENGTH: 349
<212> TYPE: PRT
<213> ORGANISM: Artificial Sequence
<220> FEATURE:
<223> OTHER INFORMATION: Amino acid sequence of full-length CTGF

<400> SEQUENCE: 9

```
Met Thr Ala Ala Ser Met Gly Pro Val Arg Val Ala Phe Val Val Leu
 1               5                  10                  15

Leu Ala Leu Cys Ser Arg Pro Ala Val Gly Gln Asn Cys Ser Gly Pro
                20                  25                  30

Cys Arg Cys Pro Asp Glu Pro Ala Pro Arg Cys Pro Ala Gly Val Ser
            35                  40                  45

Leu Val Leu Asp Gly Cys Gly Cys Cys Arg Val Cys Ala Lys Gln Leu
        50                  55                  60

Gly Glu Leu Cys Thr Glu Arg Asp Pro Cys Asp Pro His Lys Gly Leu
 65                  70                  75                  80

Phe Cys Asp Phe Gly Ser Pro Ala Asn Arg Lys Ile Gly Val Cys Thr
                85                  90                  95

Ala Lys Asp Gly Ala Pro Cys Ile Phe Gly Gly Thr Val Tyr Arg Ser
            100                 105                 110

Gly Glu Ser Phe Gln Ser Ser Cys Lys Tyr Gln Cys Thr Cys Leu Asp
        115                 120                 125

Gly Ala Val Gly Cys Met Pro Leu Cys Ser Met Asp Val Arg Leu Pro
    130                 135                 140

Ser Pro Asp Cys Pro Phe Pro Arg Arg Val Lys Leu Pro Gly Lys Cys
145                 150                 155                 160

Cys Glu Glu Trp Val Cys Asp Glu Pro Lys Asp Gln Thr Val Val Gly
                165                 170                 175

Pro Ala Leu Ala Ala Tyr Arg Leu Glu Asp Thr Phe Gly Pro Asp Pro
            180                 185                 190

Thr Met Ile Arg Ala Asn Cys Leu Val Gln Thr Thr Glu Trp Ser Ala
        195                 200                 205

Cys Ser Lys Thr Cys Gly Met Gly Ile Ser Thr Arg Val Thr Asn Asp
    210                 215                 220

Asn Ala Ser Cys Arg Leu Glu Lys Gln Ser Arg Leu Cys Met Val Arg
225                 230                 235                 240

Pro Cys Glu Ala Asp Leu Glu Glu Asn Ile Lys Gly Lys Lys Cys
                245                 250                 255

Ile Arg Thr Pro Lys Ile Ser Lys Pro Ile Lys Phe Glu Leu Ser Gly
                260                 265                 270

Cys Thr Ser Met Lys Thr Tyr Arg Ala Lys Phe Cys Gly Val Cys Thr
            275                 280                 285

Asp Gly Arg Cys Cys Thr Pro His Arg Thr Thr Thr Leu Pro Val Glu
        290                 295                 300

Phe Lys Cys Pro Asp Gly Glu Val Met Lys Lys Asn Met Met Phe Ile
305                 310                 315                 320

Lys Thr Cys Ala Cys His Tyr Asn Cys Pro Gly Asp Asn Asp Ile Phe
                325                 330                 335

Glu Ser Leu Tyr Tyr Arg Lys Met Tyr Gly Asp Met Ala
            340                 345
```

<210> SEQ ID NO 10
<211> LENGTH: 21

```
<212> TYPE: RNA
<213> ORGANISM: Artificial Sequence
<220> FEATURE:
<223> OTHER INFORMATION: Target mRNA sequence for FPRL1 siRNA

<400> SEQUENCE: 10
aauucacauc gugguggaca u                                           21

<210> SEQ ID NO 11
<211> LENGTH: 19
<212> TYPE: RNA
<213> ORGANISM: Artificial Sequence
<220> FEATURE:
<223> OTHER INFORMATION: Sense strand of luciferase siRNA, wherein
      'dTdT' is attached to 3' end

<400> SEQUENCE: 11
cguacgcgga auacuucga                                              19

<210> SEQ ID NO 12
<211> LENGTH: 19
<212> TYPE: RNA
<213> ORGANISM: Artificial Sequence
<220> FEATURE:
<223> OTHER INFORMATION: Anti-sense strand of luciferase siRNA, wherein
      'dTdT' is attached to 3' end

<400> SEQUENCE: 12
ucgaaguauu ccgcguacg                                              19

<210> SEQ ID NO 13
<211> LENGTH: 23
<212> TYPE: DNA
<213> ORGANISM: Artificial Sequence
<220> FEATURE:
<223> OTHER INFORMATION: sFPRL1 primer

<400> SEQUENCE: 13
gaccttggat tcttgctcta gtc                                         23

<210> SEQ ID NO 14
<211> LENGTH: 22
<212> TYPE: DNA
<213> ORGANISM: Artificial Sequence
<220> FEATURE:
<223> OTHER INFORMATION: asFPRL1 primer

<400> SEQUENCE: 14
ggatcagtct ctctcggaag tc                                          22

<210> SEQ ID NO 15
<211> LENGTH: 23
<212> TYPE: DNA
<213> ORGANISM: Artificial Sequence
<220> FEATURE:
<223> OTHER INFORMATION: sCTGF primer

<400> SEQUENCE: 15
ttccagagca gctgcaagta cca                                         23

<210> SEQ ID NO 16
<211> LENGTH: 23
<212> TYPE: DNA
```

```
<213> ORGANISM: Artificial Sequence
<220> FEATURE:
<223> OTHER INFORMATION: asCTGF primer

<400> SEQUENCE: 16
ttgtcattgg taacccgggt gga                                              23
```

PHARMACEUTICAL COMPOSITION USING CONNECTIVE-TISSUE GROWTH FACTOR

CROSS-REFERENCES TO RELATED APPLICATION

This application is a National Stage application of PCT/KR2011/001125 filed on Feb. 21, 2011, which claims priority to Korean Patent Application No. 10-2010-0132775 filed on Dec. 22, 2010, which claims priority to U.S. Patent Application No. 61/328,686 filed on Apr. 28, 2010, the contents of which are incorporated herein by reference.

FIELD OF THE INVENTION

This disclosure relates to an angiogenesis-related pharmaceutical composition using connective tissue growth factor, more particularly to a pharmaceutical composition for promoting angiogenesis containing the connective tissue growth factor or a pharmaceutical composition for inhibiting angiogenesis containing at least one selected from the group consisting of polypeptide, antibody and a compound binding to connective tissue growth factor.

BACKGROUND OF THE INVENTION

Angiogenesis is a process wherein new capillary vessels are formed from the existing microvessels, and angiogenesis normally occurs during embryonic development, tissue regeneration and wound healing, corpus lutem development which is periodic change in female reproductive system, and even in this case, angiogenesis is stringently controlled and progressed (Folkman J et al., Int. Rev. Exp. Pathol., 16, pp 207-248, 1976).

In the adult, vascular endothelial cells grow very slowly, and relatively do not divide well compared to other kinds of cells. The process of angiogenesis generally consists of decomposition of vascular basement membrane due to protease by stimulation of angiogenesis promoter, migration of vascular endothelial cells, proliferation, and tube formation by differentiation of vascular endothelial cells to reconstitute blood vessels to produce new capillary vessels.

There are diseases caused by failing to self-regulation of angiogenesis and abnormal growth. The diseases related to angiogenesis occurring at pathological states include hemangioma, vascular fibroma, vascular malformation, and cardiovascular disease such as atherosclerosis, vascular adhesion, scleroderma, and ophthalmic diseases caused by angiogenesis include angiogenesis due to corneal transplantation, neovascular glaucoma, diabetic retinopathy, corneal disease caused by angiogenesis, macular degeneration, pterygium, retinal degeneration, retrolental fibroplasias, granular conjunctivitis, and the like.

Chronic inflammatory diseases such as arthritis, dermatological diseases such as psoriasis, capillarectasia, pyogenic granuloma, seborrheic dermatitis, acne, Alzheimer's diseases and obesity are also related to angiogenesis, and cancer growth and metastasis are necessarily dependent upon antiogenesis (D'Amato R J et al., Ophthalmology, 102(9), pp 1261-1262, 1995; Arbiser J L, J. Am. Acad. Dermatol., 34(3), pp 486-497, 1996; O'Brien K D et al. Circulation, 93(4), pp 672-682, 1996; Hanahan D et al., Cell, 86, pp 353-364, 1996).

Particularly, in cancer, angiogenesis plays an important function for cancer cell growth and metastasis. Tumor is supplied with nutrient and oxygen required for growth through angiogenesis, and angiogenetic blood vessels penetrated into tumor provide a pathway for cancer cells to enter into blood circulation system thereby allowing metastasis of cancer cells (Folkman and Tyler, Cancer Invasion and metastasis, Biologic mechanisms and Therapy (S. B. Day ed.) Raven press, New York, pp 94-103, 1977; Polverini P J, Crit. Rev. Oral. Biol. Med., 6(3), pp 230-247, 1995).

To the contrary, although excessive formation of blood vessels sometime becomes a leading cause of worsening of diseases, non-formation of blood vessels also becomes a cause of serious diseases. Angiogenesis is essential phenomenon for wound healing or tissue regeneration, for example, placenta with undeveloped blood vessel formation is an important cause of miscarriage, and necrosis, ulcer and ischemia due to non-formation of blood vessel may induce abnormal function of tissues or organs or may become a cause of death. And, diseases such as atherosclerosis, myocardial infarction and angina pectoris also become a cause of slow blood supply. Accordingly, there is a need for development of a treatment method that may decrease tissue damage due to low oxygen or low nutrition state caused by non-formation of blood vessels, and induce or promote new blood vessel formation for smooth tissue regeneration.

DETAILED DESCRIPTION OF THE INVENTION

Technical Problem

The inventors found out that in angiogenesis in which a kind of inflammatory cytokine, vascular endothelial growth factor-A (VEGF-A), and FPRL1 (formyl peptide receptor-like 1) are involved, connective tissue growth factor (CTGF) binds to FPRL1 to induce angiogenesis, particularly found out a region where CTGF binds to FPRL1, confirmed that angiogenesis is induced through the region, and completed the invention.

Therefore, one embodiment of the present invention provides a pharmaceutical composition for promoting angiogenesis containing a fragment of protein corresponding to a FPRL1 binding region in CTGF and/or gene encoding the same; use of a fragment of protein corresponding to a FPRL1 binding region in CTGF and/or gene encoding the same for promoting angiogenesis and/or preparing angiogenesis promoter; and a method for promoting angiogenesis comprising administering a fragment of protein corresponding to a FPRL1 binding region in CTGF and/or gene encoding the same to a patient in need of promoting angiogenesis.

Another embodiment of the present invention provides a pharmaceutical composition for inhibiting angiogenesis containing a fragment of protein corresponding to a FPRL1 binding region in CTGF and/or gene encoding the same; use of a fragment of protein corresponding to a FPRL1 binding region in CTGF and/or gene encoding the same for inhibiting angiogenesis and/or preparing angiogenesis inhibitor; and/or a method for inhibiting angiogenesis comprising administering a fragment of protein corresponding to a FPRL1 binding region in CTGF and/or gene encoding the same to a patient in need of inhibiting angiogenesis.

Yet another embodiment of the present invention provides a method for screening angiogenesis inhibitor using a FPRL1 binding region in CTGF as a target.

Technical Solution

To solve the problem, one embodiment of the invention provides a pharmaceutical composition for promoting angiogenesis containing a fragment of connective tissue growth factor protein comprising continuous 38 or more amino acids, for example continuous 38 to 140 amino acids (for example, selected from regions from 103$^{rd}$ to 242$^{nd}$ amino acid), continuous 38 to 100 amino acids (for example, selected from regions from 103$^{rd}$ to 202$^{nd}$ amino acid), or continuous 38 to 80 amino acids (for example, selected from regions from 163$^{rd}$ to 242$^{nd}$ amino acid), preferably continuous 38 to 39 amino acids, which comprises amino acid sequence of SEQ ID NO. 5 (WVCDEPKDQTVVGPALAAYRLEDTFGP-DPTMIRANCLV), which is a region from 164$^{th}$ to 201$^{st}$ amino acid, in the amino acid sequence of SEQ ID NO. 9; use of the fragment of connective tissue growth factor protein for promoting angiogenesis and/or preparing angiogenesis promoter; and a method for promoting angiogenesis comprising administering the fragment of connective tissue growth factor protein to a patient in need of promoting angiogenesis.

Another embodiment provides a pharmaceutical composition for promoting angiogenesis containing gene encoding a fragment of connective tissue growth factor protein comprising continuous 38 or more amino acids, for example, continuous 38 to 140 amino acids (for example, selected from regions from 103$^{rd}$ to 242$^{nd}$ amino acid), continuous 38 to 100 amino acids (for example, selected from regions from 103$^{rd}$ to 202$^{nd}$ amino acid), or continuous 38 to 80 amino acids (for example, selected from regions from 163$^{rd}$ to 242$^{nd}$ amino acid), preferably continuous 38 to 39 amino acids, which comprises amino acid sequence of SEQ ID NO. 5, in amino acid sequence of SEQ ID NO. 9; use of the gene encoding a fragment of connective tissue growth factor protein for promoting angiogenesis and/or preparing angiogenesis promoter; and a method for promoting angiogenesis comprising administering the gene encoding a fragment of connective tissue growth factor protein to a patient in need of promoting angiogenesis.

The method for promoting angiogenesis may further include confirming a patient in need of promoting angiogenesis, before the administration, wherein the patient in need of promoting angiogenesis may be a patient requiring prevention or treatment of angina pectoris, atherosclerosis, stroke, vascular dementia, chronic ulcer, or wound. The patient may be mammals, preferably human.

Yet another embodiment provides a pharmaceutical composition for inhibiting angiogenesis containing at least one selected from the group consisting of polypeptide, antibody and a compound binding to a fragment of connective tissue growth factor protein comprising continuous 38 or more amino acids, for example, continuous 38 to 140 amino acids (for example, selected from regions from 103$^{rd}$ to 202$^{nd}$ amino acid), continuous 38 to 100 amino acids (For example, selected from regions from 103$^{rd}$ to 202$^{nd}$ amino acid), or continuous 38 to 80 amino acids (for example, selected from regions from 163$^{rd}$ to 242$^{nd}$ amino acid), preferably 38 to 39 amino acids, which comprises amino acid sequence of SEQ ID NO. 5, in amino acid sequence of SEQ ID NO. 9; use of the polypeptide, antibody and compound binding to the fragment of connective tissue growth factor protein for inhibiting angiogenesis and/or preparing angiogenesis inhibitor; and a method for inhibiting angiogenesis comprising administering the polypeptide, antibody and compound binding to the fragment of connective tissue growth factor protein to a patient in need of inhibiting angiogenesis.

Yet another embodiment provides a pharmaceutical composition for inhibiting angiogenesis containing an expression inhibitor of a fragment of connective tissue growth factor comprising continuous 38 or more amino acids, for example, continuous 38 to 140 amino acids (for example, selected from regions from 103$^{rd}$ to 202$^{nd}$ amino acid), continuous 38 to 100 amino acids (For example, selected from regions from 103$^{rd}$ to 202$^{nd}$ amino acid), or continuous 38 to 80 amino acids (for example, selected from regions from 163$^{rd}$ to 242$^{nd}$ amino acid), preferably 38 to 39 amino acids, which comprises amino acid sequence of SEQ ID NO. 5, in amino acid sequence of SEQ ID NO. 9, as an active ingredient; use of an expression inhibitor of the fragment of connective tissue growth factor protein for inhibiting angiogenesis and/or preparing angiogenesis inhibitor; and a method for inhibiting angiogenesis comprising administering an expression inhibitor of a fragment of connective tissue growth factor protein to a patient in need of inhibiting angiogenesis. For example, the expression inhibitor may be at least one selected from the group consisting of antisense nucleotide, short interfering RNA, and short hairpin RNA, which complementarily bind to the base sequence (SEQ ID NO. 7) of gene encoding the amino acid sequence of SEQ ID NO. 5 or mRNA thereof, for example, base sequence consisting of continuous 15 to 30, preferably continuous 20 to 25 bases in the mRNA.

The method for inhibiting angiogenesis may further include confirming a patient in need of inhibiting angiogenesis, before the administration, wherein the patient in need of inhibiting angiogenesis may be a patient requiring prevention or treatment of cancer growth and metastasis, rheumatoid arthritis, psoriasis, diabetic retinopathy, diabetic nephropathy, hypertension, endometriosis, adiposis, retinopathy of prematurity, corneal inflammation rejection, neovascular glaucoma, proliferative retinopathy, hemophilic arthropathy, keloid, wound granulation, vascular adhesion, osteoarthritis, Crohn's disease, restenosis, atherosclerosis, intestinal adhesion, ulcer, liver cirrhosis, neophritis, malignant nephrosclerosis, organ transplant rejection, glomerulopathy, diabetes mellitus, or inflammation. The patient may be mammals, preferably human.

Yet another embodiment provides a method for screening angiogenesis inhibitor comprising (a) treating cells comprising gene encoding a fragment of connective tissue growth factor protein comprising continuous 38 or more amino acids, for example, continuous 38 to 140 amino acids (for example, selected from regions from 103$^{rd}$ to 202$^{nd}$ amino acid), continuous 38 to 100 amino acids (For example, selected from regions from 103$^{rd}$ to 202$^{nd}$ amino acid), or continuous 38 to 80 amino acids (for example, selected from regions from 163$^{rd}$ to 242$^{nd}$ amino acid), preferably 38 to 39 amino acids, which comprises amino acid sequence of SEQ ID NO. 5, in amino acid sequence of SEQ ID NO. 9, with a candidate compound; and (b) measuring the degree of expression of the gene, wherein if the degree of expression of the gene is decreased in the cells treated with the candidate compound, compared to the cells that is not treated with the candidate compound, the candidate material is determined as angiogenesis inhibitor.

Hereinafter, the present invention will be explained in detail.

The composition for promoting angiogenesis contains a fragment of connective tissue growth factor protein comprising continuous 38 or more amino acids, for example, continuous 38 to 140 amino acids (for example, selected from regions from 103$^{rd}$ to 242$^{nd}$ amino acid), continuous 38 to 100 amino acids (for example, selected from regions from 103$^{rd}$ to 202$^{nd}$ amino acid), or continuous 38 to 80 amino acids (for example, selected from regions from 163$^{rd}$ to 242$^{nd}$ amino acid), preferably continuous 38 to 39 amino acids, which comprises amino acid sequence of SEQ ID NO. 5, in amino acid sequence of SEQ ID NO. 9.

Full length amino acid sequence of the connective tissue growth factor (CTGF) may be derived from human (for example, accession no. CAG46559.1), and represented by SEQ ID NO. 9. In angiogenesis in which a kind of inflammatory cytokine, vascular endothelial growth factor-A (VEGF-A) and FPRL1 (formyl peptide receptor-like 1) are involved, the connective tissue growth factor protein may bind to FPRL1 to induce angiogenesis. Specifically, the connective tissue growth factor has activity for inducing FPRL1-specific ERK phosphorylation (see Experiment result 2), is a protein of which expression is induced by VEFG-A (see Experiment result 3), and it binds to FPRL1 to induce angiogenesis (see Experiment result 11).

Particularly, a region where the connective tissue growth factor protein binds to FPRL1 is a region from $164^{th}$ amino acid to $201^{st}$ amino acid in SEQ ID NO. 9 which is full length amino acid sequence of connective tissue growth factor protein, and it may be represented by amino acid sequence of SEQ ID NO. 5 (see Experiment result 4).

Therefore, the fragment of connective tissue growth factor protein, which is an active ingredient of the pharmaceutical composition for promoting angiogenesis of the present invention, may comprise continuous 38 or more amino acids, for example, continuous 38 to 140 amino acids (for example, selected from regions from $103^{rd}$ to $242^{nd}$ amino acid), continuous 38 to 100 amino acids (for example, selected from regions from $103^{rd}$ to $202^{nd}$ amino acid), or continuous 38 to 80 amino acids (for example, selected from regions from $163^{rd}$ to $242^{nd}$ amino acid), preferably continuous 38 to 39 amino acids, which comprises amino acid sequence of SEQ ID NO. 5, a region from $164^{th}$ amino acid to $201^{st}$ amino acid in SEQ ID NO. 9, in the amino acid sequence of SEQ ID NO. 9 which is full length sequence of the connective tissue growth factor protein. The fragment of connective tissue growth factor protein may be preferably represented by amino acid sequence of SEQ ID NO. 6 (EWVCDEPKDQTV-VGPALAAYRLEDTFGPDPTMIRANCLV), but not limited thereto.

The fragment of connective tissue growth factor protein is a binding region to FPRL1 (see Experiment result 5), effectively induces FPRL1-specific ERK phosphorylation (see Experiment result 6), activates FPRL1 to increase intracellular $Ca^{2+}$ concentration (see Experiment result 7), and finally, effectively induces angiogenesis (see Experiment result 9).

The pharmaceutical composition for promoting angiogenesis of the present invention may contain gene encoding connective tissue growth factor protein comprising continuous 38 or more amino acids, for example, continuous 38 to 140 amino acids (for example, selected from regions from $103^{rd}$ to $242^{nd}$ amino acid), continuous 38 to 100 amino acids (for example, selected from regions from $103^{rd}$ to $202^{rd}$ amino acid), or continuous 38 to 80 amino acids (for example, selected from regions from $163^{rd}$ to $242^{nd}$ amino acid), preferably continuous 38 to 39 amino acids, which comprises amino acid sequence of SEQ ID NO. 5, in the amino acid sequence of SEQ ID NO. 9. The gene may preferably encode amino acid sequence of SEQ ID NO. 5, a region from $164^{th}$ amino acid to $201^{st}$ amino acid in the full length amino acid sequence of connective tissue growth factor protein, or encode amino acid sequence of SEQ ID NO. 6 comprising the amino acid sequence of SEQ ID NO. 5, but is not limited thereto. More preferably, the gene may be represented by base sequence of SEQ ID NO. 7 encoding the amino acid sequence of SEQ ID NO. 5 (164-TGG GTG TGT GAC GAG CCC AAG GAC CAA ACC GTG GTT GGG CCT GCC CTC GCG GCT TAC CGA CTG GAA GAC ACG TTT GGC CCA GAC CCA ACT ATG ATT AGA GCC AAC TGC CTG GTC-201), and it may be represented by base sequence of SEQ ID NO. 8 encoding the amino acid sequence of SEQ ID NO. 6 (163-GAG TGG GTG TGT GAC GAG CCC AAG GAC CAA ACC GTG GTT GGG CCT GCC CTC GCG GCT TAC CGA CTG GAA GAC ACG TTT GGC CCA GAC CCA ACT ATG ATT AGA GCC AAC TGC CTG GTC-201).

The gene may be inserted into a vector, preferably recombinant expression vector, but is not limited thereto, wherein the recombinant expression vector may comprise the gene and expression regulator including operably linked promoter, and the like. For example, the recombinant expression vector may be, for example, EcoR I-INSERT-Xba I in pAB-Bee™-FH vector (including signal peptide & flag tag), but is not limited thereto.

Specifically, the vector is used for a nucleic acid molecule transferring a DNA fragment from one cell to another cell, and may be derived from those selected from the group consisting of plasmid, bacteriophage, and plant and animal virus, but is not limited thereto.

The expression vector refers to recombinant DNA comprising aimed coding sequence and appropriate nucleic acid sequence required for expression of the coding sequence, operably linked in a specific host, and in general, nucleic acid sequence required for expression in prokaryotic cells may comprise promoter, operator (optional), and ribosome binding region, in addition to the other sequence, and eukaryotic cells use promoter, enhancer, and stop and polyadenylation signal, which are known in the art.

The recombinant expression vector may be a genetic construct comprising operably linked essential regulator elements so as to express the gene, which may prepare aimed protein, a fragment of connective tissue growth factor in the present invention, in a suitable host cells.

The term "operably linked" means that nucleic acid expression regulator sequence and nucleic acid sequence encoding aimed protein are functionally linked so as to perform general functions. For example, promoter and nucleic acid encoding protein or RNA may be operably linked to influence on the expression of coding sequence. The operable link with recombinant vector may be prepared using gene recombination technology well known in the art, and site-specific DNA cleavage and ligation may be performed using enzyme, and the like generally known in the art.

Suitable expression vector comprises expression regulatory elements such as promoter, initiation codon, stop codon, polyadehylation signal and enhancer, and the like, and it may be variously prepared according to the purpose. The initiation codon and stop codon should act in the individual when a genetic construct is administered, and it should be in frame with coding sequence.

The pharmaceutical composition for promoting angiogenesis may be used for treatment of diseases caused by inhibition of angiogenesis or diseases that may be cured by promoting angiogenesis, but is not limited thereto, and for example, it may be used for treatment of angina pectoris, atherosclerosis, ischemic stroke, vascular dementia, chronic ulcer, or wound. Thus, yet another embodiment of the present invention provides a composition for prevention and/or treatment of angina pectoris, atherosclerosis, ischemic stroke, vascular dementia, chronic ulcer, or wound, comprising the pharmaceutical composition for promoting angiogenesis as an active ingredient.

Meanwhile, the pharmaceutical composition for inhibiting angiogenesis contains at least one selected from the group consisting of polypeptide, antibody and a compound, which bind to a fragment of connective tissue growth factor protein comprising continuous 38 or more amino acids, for example, continuous 38 to 140 amino acids (for example, selected from regions from $103^{rd}$ to $242^{nd}$ amino acid), continuous 38 to 100 amino acids (for example, selected from regions from $103^{rd}$ to $202^{nd}$ amino acid), or continuous 38 to 80 amino acids (for example, selected from regions from 163$^{rd}$ to 242$^{rd}$ amino acid), preferably continuous 38 to 39 amino acids, which comprises amino acid sequence of SEQ ID NO. 5, in the amino acid sequence of SEQ ID NO. 9

As described, since a fragment of connective tissue growth factor protein comprising continuous 38 or more amino acids, for example, continuous 38 to 140 amino acids (for example, selected from regions from 103$^{rd}$ to 242$^{nd}$ amino acid), continuous 38 to 100 amino acids (for example, selected from regions from 103$^{rd}$ to 202$^{nd}$ amino acid), or continuous 38 to 80 amino acids (for example, selected from regions from 163$^{rd}$ to 242$^{nd}$ amino acid), preferably continuous 38 to 39 amino acids, which comprises amino acid sequence of SEQ ID NO. 5, in SEQ ID NO. 9 which is amino acid sequence of full length protein of connective tissue growth factor, binds to FPRL1 to induce angiogenesis, at least one selected from the group consisting of polypeptide, antibody and a compound binding to the fragment of connective tissue growth factor protein may effectively inhibit angiogenesis.

The fragment of connective tissue growth factor may comprise continuous 38 or more amino acids, for example, continuous 38 to 140 amino acids (for example, selected from regions from 103$^{rd}$ to 242$^{nd}$ amino acid), continuous 38 to 100 amino acids (for example, selected from regions from 103$^{rd}$ to 202$^{nd}$ amino acid), or continuous 38 to 80 amino acids (for example, selected from regions from 163$^{rd}$ to 242$^{nd}$ amino acid), preferably continuous 38 to 39 amino acids, which comprises amino acid sequence of SEQ ID NO. 5, a 164$^{th}$ to 201$^{st}$ region, in the amino acid sequence of SEQ ID NO. 9 which is full length sequence of the connective tissue growth factor protein, and more preferably, it may be represented by amino acid sequence of SEQ ID NO. 6 comprising the amino acid sequence of SEQ ID NO. 5.

Since the fragment of connective tissue growth factor protein comprises a FPRL1-binding region, polypeptide, antibody or a compound binding to the fragment of connective tissue growth factor protein may block binding of the connective tissue growth factor protein to FPRL1 to effectively inhibit angiogenesis.

The polypeptide, antibody or compound is not specifically limited as long as it may bind to the fragment of connective tissue growth factor protein, but preferably, it may be one binding to amino acid sequence of SEQ ID NO. 6, or SEQ ID NO. 5, and it may be easily prepared by one of ordinary knowledge in the art according to the amino acid sequence of the fragment of connective tissue growth factor protein to be bound.

Furthermore, pharmaceutical composition for inhibiting angiogenesis may contain at least one selected from the group consisting of antisense nucleotide, short interfering RNA, and short hairpin RNA, which complementarily bind to gene encoding a fragment of connective tissue growth factor protein comprising continuous 38 or more amino acids, for example, continuous 38 to 140 amino acids (for example, selected from regions from 103$^{rd}$ to 242$^{nd}$ amino acid), continuous 38 to 100 amino acids (for example, selected from regions from 103$^{rd}$ to 202$^{nd}$ amino acid), or continuous 38 to 80 amino acids (for example, selected from regions from 163$^{rd}$ to 242$^{nd}$ amino acid), preferably continuous 38 to 39 amino acids, comprising amino acid sequence of SEQ ID NO. 5, in the amino acid sequence of SEQ ID NO. 9, or mRNA thereof, for example, base sequence consisting of continuous 15 to 30, preferably continuous 20 to 25 bases in the mRNA.

The siRNA comprises a sense RNA strand and a complementary antisense RNA strand, the two strands anneal each other by standard Watson-Crick base pair interaction, and the sense strand comprises identical nucleic acid sequence to the target sequence in target mRNA. Technologies of selecting the target sequence of siRNA are described in, for example, Tuschl T et al, "The siRNA User Guide" revised Oct. 11, 2002.

The sense and antisense strands of the siRNA may comprise two complementary single-stranded RNA molecules, or it may comprise single molecule wherein two complementary parts form a base pair and covalently bonded by a "hairpin" region of single strand. The latter is referred to as short hairpin RNA (shRNA), wherein the shRNA is a single strand and forms a stem-loop structure in vivo. The shRNA is generally synthesized by transcription of complementary DNA sequence from Pol III promoter in vivo. Pol-III-induced transcription starts at a well-defined start site and stops at a linear (-TTTT-) second residue consisting of 4 or more thymidines to produce non-poly(A) transcript. Pol III promoter may be activated in all cells, and it may express shRNA. After transcription, the loop of shRNA is cleaved by dicer, and the shRNA acts with RISC(RNA-induced silencing complex) like siRNA (see, Tuschl, T. (2002), Cell 110(5): 563-74).

The siRNA may be obtained using many technologies known to one of ordinary knowledge in the art. For example, siRNA may be chemically synthesized using a method known in the art or produced by recombination. Preferably, the siRNA may be chemically synthesized using suitably protected ribonucleoside phosphoramidites and the existing DNA/RNA synthesizer. The siRNA may be synthesized as two complementary and separated RNA molecules or one RNA molecule having two complementary regions. Alternatively, the siRNA may be expressed from recombinant DNA plasmid using suitable promoter. The promoter suitable for expressing the siRNA from plasmid may include, for example, U6 or H1 RNA pol III promoter sequence and cytomegalovirus promoter. And, the recombinant plasmid may include inductive or controllable promoter in order to express siRNA in a specific tissue or specific intracellular environment.

The siRNA may be expressed as two complementary and separated RNA molecule or one RNA molecule having two complementary regions from recombinant plasmid. The selection of suitable plasmid for expression of siRNA, a method of inserting nucleic acid into plasmid to express siRNA, and a method of transferring recombinant plasmid to aimed cells are within the scope of technologies in the field to which the invention pertains. For example, see [Tuschl, T. (2002), Nat. Biotechnol, 20: 446-448]; [Brummelkamp T R et al. (2002), Science 296: 550-553]; [Miyagishi M et al. (2002), Nat. Biotechnol. 20: 497-500]; [Paddison P J et al. (2002), Genes Dev. 16: 948-958; Lee N S et al. (2002), Nat. Biotechnol. 20: 500-505]; and [Paul C P et al. (2002), Nat. Biotechnol. 20: 505-508], which references are incorporated herein by reference.

For example, according to one embodiment of the invention, as the siRNA of FPRL1, double stranded RNA molecule with target of AAUUCACAUCGUGGUGGACAU (SEQ ID NO. 10) (for example, Sense: UUCACAUCGUGGUGGA-CAUdTdT (SEQ ID NO. 3) and Anti-sense: AUGUCCAC-CACGAUGUGAAdTdT (SEQ ID NO. 4)) may be used.

The pharmaceutical composition for inhibiting angiogenesis may be used for prevention and/or treatment of angiogenesis-related diseases. The angiogenesis-related diseases may be diseases or conditions selected from the group consisting of cancer growth and metastasis, rheumatoid arthritis, psoriasis, diabetic retinopathy, diabetic nephropathy, hypertension, endometriosis, adiposis, retinopathy of prematurity, corneal inflammation rejection, neovascular glaucoma, proliferative retinopathy, hemophilic arthropathy, keloid, wound granulation, vascular adhesion, osteoarthritis, Crohn's disease, restenosis, atherosclerosis, intestinal adhesion, ulcer, liver cirrhosis, neophritis, malignant nephrosclerosis, organ transplant rejection, glomerulopathy, diabetes mellitus, inflammation, and the like. Thus, one embodiment of the present invention provides a composition for prevention or treatment of disease or condition selected from the group consisting of cancer growth and metastasis, rheumatoid arthritis, psoriasis, diabetic retinopathy, diabetic nephropathy, hypertension, endometriosis, adiposis, retinopathy of prematurity, corneal inflammation rejection, neovascular glaucoma, proliferative retinopathy, hemophilic arthropathy, keloid, wound granulation, vascular adhesion, osteoarthritis, Crohn's disease, restenosis, atherosclerosis, intestinal adhesion, ulcer, liver cirrhosis, neophritis, malignant nephrosclerosis, organ transplant rejection, glomerulopathy, diabetes mellitus, inflammation, and the like, containing the pharmaceutical composition for inhibiting angiogenesis as an active ingredient.

To administer the pharmaceutical composition for promoting angiogenesis or pharmaceutical composition for inhibiting angiogenesis, at least one kind of pharmaceutically acceptable carrier may be further included in addition to the above described active ingredient. The pharmaceutically acceptable carrier may be at least one selected from a saline solution, sterile water, Ringer's solution, buffered saline, dextrose solution, maltodextrin solution, glycerol, ethanol, liposome, and a mixture thereof, and if necessary, other common additives such as antioxidant, buffer solution, bacteriostatic agent, and the like may be added. And, diluents, dispersant, surfactant, binder and lubricant may be additionally added to formulated into a dosage form for injection such as an aqueous solution, suspension, emulsion, and the like, a pill, a capsule, granules or a tablet, and a target organ-specific antibody or other ligands may be bound to the carrier so as to specifically act on a target organ. Furthermore, the pharmaceutical composition may be preferably formulated according to diseases or ingredients by suitable method in the art or using a method disclosed in Remington's Pharmaceutical Science (Recent Edition), Mack Publishing Company, Easton Pa.

The pharmaceutical composition for promoting angiogenesis or pharmaceutical composition for inhibiting angiogenesis of the present invention may be prepared for oral, topical, parenteral, intravenous, intramuscular, subcutaneous, intraocular, transdermal administration, and the like. Preferably, it may be used in an injectable form.

Thereby, it may be mixed with pharmaceutically acceptable medium for injectable composition to directly inject into an area to be treated. The composition of the present invention may comprise a lyophilized composition that enables composition of an injectable solution upon addition of an isotonic sterile solution, sterile water or suitable physiological saline. Direct injection into tumor of a patient is favorable because treatment efficiency is focused on the infected tissue. The used dose may be controlled by various parameters, particularly, gene, vector, used administration route, disease in question or alternatively, required treatment period. And, the range may be varied according to weight, age, gender, health condition, diet of a patient, administration time, administration route, excretion rate and severance of disease, and the like. The daily dose may be about 0.0001 to 10 mg/kg, preferably 0.001 to 1 mg/kg, and it may be preferable to administer one time or divide into several times a day.

Meanwhile, a method for screening angiogenesis inhibitor comprises (a) treating cells comprising gene encoding a fragment of connective tissue growth factor protein comprising continuous 38 or more amino acids, for example, continuous 38 to 140 amino acids (for example, selected from regions from $103^{rd}$ to $202^{nd}$ amino acid), continuous 38 to 100 amino acids (For example, selected from regions from $103^{rd}$ to $202^{rd}$ amino acid), or continuous 38 to 80 amino acids (for example, selected from regions from $163^{rd}$ to $242^{nd}$ amino acid), preferably 38 to 39 amino acids, which comprises amino acid sequence of SEQ ID NO. 5, in amino acid sequence of SEQ ID NO. 9, with a candidate compound; and (b) measuring the degree of expression of the gene, wherein if the degree of expression of the gene is decreased in the cells treated with the candidate compound, compared to the cells that are not treated with the candidate compound, the candidate material is determined as angiogenesis inhibitor.

In the step (a), the fragment of connective tissue growth factor protein may be represented by amino acid sequence of SEQ ID NO. 5 or SEQ ID NO. 6. The candidate compound may be peptide, protein, a non-peptide compound, a synthetic compound, a fermentation product, cell extract, plant extract, or animal extract, but is not limited thereto, and it may include those widely known as well as novel material. In the step (a), the cells may be transformed cells with recombinant expression vector comprising the gene, and the transformation method is well known in the art.

In the step (b), the degree of expression of gene may be preferably measured by immunofluorescence method, enzyme-linked immunosorbent assay (ELISA), Western Blotting or RT-PCR, but is not limited thereto. In case antibody is used for confirming the amount of protein according to the expression, a secondary antibody specific to target protein and linked to detectable label may be added, and after adding the secondary antibody, a tertiary antibody having binding affinity to the secondary antibody and linked to detectable label may be added. As the detectable label in the secondary or tertiary antibody, enzyme exhibiting coloration when cultured and appropriate coloring substrate may be used. The detectable part may include a composition detectable by spectroscopic, enzymatic, photochemical, bioelectronical, immunochemical, electrical, optical or chemical means, and for example, it may include fluorescent marker and dye, magnetic label, linked enzyme, mass spectrometric tag, spin tag, electron donor and receptor, but is not limited thereto.

If the degree of expression of the gene is decreased in the cells treated with the candidate compound, compared to control that is not treated with the candidate compound, the candidate compound may be selected as angiogenesis inhibitor. The angiogenesis inhibitor may be used for prevention or treatment of disease or condition selected from the group consisting of rheumatoid arthritis, psoriasis, diabetic retinopathy, diabetic nephropathy, hypertension, endometriosis, adiposis, cancer, retinopathy of prematurity, corneal inflammation rejection, neovascular glaucoma, proliferative retinopathy, hemophilic arthropathy, keloid, wound granulation, vascular adhesion, osteoarthritis, Crohn's disease, restenosis, atherosclerosis, intestinal adhesion, ulcer, liver cirrhosis, neophritis, malignant nephrosclerosis, organ transplant rejection, glomerulopathy, diabetes mellitus, inflammation, and the like, but is not limited thereto.

Using the screening method of the present invention, a therapeutic agent involved in the mechanism may be selected within a short time, and through experiments for the provement, useful prevention and/or treatment agent may be provided to a patient in need of prevention and/or treatment of disease caused by angiogenesis.

The fragment of connective tissue growth factor protein, which is discovered in the present invention, is a binding region to FPRL1, effectively induces FPRL1-specific ERK phosphorylation, activates FPRL1 to increase intracellular $Ca^{2+}$ concentration, and finally, effectively induces angiogenesis, and thus, the fragment of connective tissue growth factor protein may be useful for a pharmaceutical composition for promoting angiogenesis, while polypeptide, antibody or a compound binding to the fragment of connective tissue growth factor protein may be useful for a pharmaceutical composition for inhibiting angiogenesis.

BRIEF DESCRIPTION OF DRAWINGS

FIG. 4 shows the results of MS/MS analysis for B12 fraction of conditioned medium.

FIG. 5 shows the results of analyzing the degree of CTGF expression in cell lysate or conditioned medium of HUVECs treated with VEGF-A according to treatment time of VEGF-A.

EXAMPLES

Figure 1:
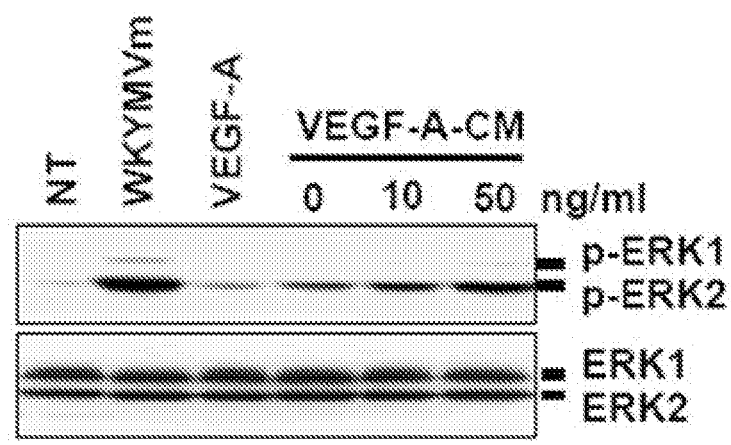
FIG. 1 shows the results of immunoblotting to confirm whether conditioned medium of HUVECs obtained by treating with VEGF-A induces ERK phosphorylation in FPRL1-overexpressed FPRL1/RBL cells.

Hereinafter, the present invention will be explained in detail with reference to the following Examples.

However, these examples are only to illustrate the invention, and the scope of the invention is not limited thereto.

In the following Examples, all data are represented by mean±standard deviation, statistically compared by Student's t test, and it is considered as being statistically significant when $p<0.05$.

<Experiment Method>
1. Experiment Material

Phospho-ERK1/2 ($Thr^{202}/Tyr^{204}$) and ERK1/2 antibody were purchased from Cell Signaling Technology Inc. (Beverly, Mass., USA), and Human CTGF antibody and anti-Flag antibody were respectively purchased from Abcam (Cambridge, Mass., USA) and Sigma Co. (St. Louis, Mo., USA). Recombinant human CTGF was purchased from BioVendor Laboratory Medicine Inc. (Brno, Czech Republic). Recombinant human VEGF-A165, anti-VEGF-A mAb, anti-VEGFR-1 mAb, and anti-VEGFR-2 mAb were obtained from R&D Systems Inc. (Minneapolis, Minn., USA).

The siRNA to FPRL1 (sense: UUCACAUCGUGGUG-GACAUdTdT (SEQ ID NO. 3), anti-sense: AUGUCCAC-CACGAUGUGAAdTdT (SEQ ID NO. 4)) and siRNA to luciferase (sense: CGUACGCGGAAUACUUCGAdTdT (SEQ ID NO. 11), anti-sense: UCGAAGUAUUC-CGCGUACGdTdT (SEQ ID NO. 12)) were synthesized in Dharmacon Research, Inc. (Chicago, Ill.). And, WKYMVm (SEQ ID NO. 1), WRWWWW (SEQ ID NO. 2, WRW4), and biotinylated WKYMVm were synthesized in A&PEP Inc (Seoul, Korea), of which purities were greater than 95%. Linker polypeptide comprising amino acid sequence of human CTGF link region (EWVCDEPKDQTVVGPA-LAAYRLEDTFGPDPTMIRANCLV (SEQ ID NO. 6)-NH$_2$) was synthesized in Anygen Co. Ltd. (Gwangjoo, Korea), of which purity was about 99.1%.

2. Cell Culture

Human umbilical vein endothelial cells (HUVECs) were treated with collagenase (Sigma, St. Louis, Mo., USA) to separate from umbilical cord (ST. MARY'S Hospital, Seoul, Korea) according to a method known in the art (Ferrero, E. et al. Transendothelial migration leads to protection from starvation-induced apoptosis in CD34+CD14+ circulating precursors: evidence for PECAM-1 involvement through Akt/PKB activation. Blood 101, 186-193, 2003). The separated HUVECs were cultured in a dish coated with 0.2% (w/v) gelatin using Medium 199 (containing 20% (v/v) of thermally inactivated fetal bovine serum and 1% (w/v) of penicillin/streptomycin).

For this experiment, each cell was cultured to subconfluence state, and those of 3 to 5 passages were used. FPRL1-expressing rat basophil leukemia (RBL)-2H3 (FPRL1/RBL) cells, FPR-expressing RBL-2H3 (FPR/RBL) cells, and RBL-2H3 (vector/RBL) cells (cells wherein FPRL1 or FPR receptor is not overexpressed) (ATCC, Manassas, Va., USA) were maintained in DMEM medium (Sigma, St. Louis, Mo., USA) containing high concentration of glucose, to which 1% penicillin/streptomycin, 20% (v/v) thermally inactivated fetal bovine serum and G418 (Geneticin) (500 ug/ml) were added. The cells were cultured at 37° C. in 5% $CO_2$.

3. Conditioned Medium

Conditioned medium was obtained from HUVECs (3 to 5 passages) cultured in Medium 199 that does not include FBS. The conditioned medium was centrifuged to remove residual cells, and it was stored at −80° C. until used.

4. Western Blot Analysis

Vector/RBL cells, FPR/RBL cells, FPRL1/RBL cells, and HUVECs were cultured to confluence, and serum-starved. The stimulated cells (1×10$^5$ cells) were washed with PBS twice, dissolved in 1 ml of sample buffer (50 mM Tris-HCl, 100 mM NaCl, 0.1% SDS, 1% Nonidet P-40, 50 mM NaF, 1 mM Na$_3$VO$_4$, 1 µg/ml aprotinin, 1 µg/ml pepstatin, and 1 µg/ml leupeptin), heated at 95° C. for 30 seconds, separated with SDS-PAGE, and then, transferred to a nitrocellulose film. Immunoblot was conducted using anti-phospho-ERK (extracellular signal regulated kinase)1/2 (Thr$^{202}$/Tyr$^{204}$) (Cell Signaling Technology, Beverly, Mass., USA), anti-ERK1/2 (Cell Signaling Technology, Beverly, Mass., USA), anti-CTGF (Abcam, Cambridge, Mass., USA), anti-Actin (Sigma, St. Louis, Mo., USA), or anti-Flag (Sigma, St. Louis, Mo., USA) antibody, and then, the film was visualized with a chemiluminescence substrate (Amersham Pharmacia).

5. Identification of FPRL1(Formyl Peptide Receptor-Like 1) Activating Protein

The conditioned medium (CM) obtained in HUVEC was loaded in HLB cartridge (waters), and separated using revere phase (RP) C18 column. The RP C18 HPLC column (218 TP5215; 2.1 mm×150 mm, Vydac) was equilibrated with water/0.1% (w/v) TFA. By concentration gradient of ACN/0.1% (w/v) TFA from 0% (w/v) to 100% (w/v), 150 ul of fraction was obtained. The obtained activated fraction was treated with trypsin and cultured at 37° C. overnight.

To obtain MS and MS/MS data of the activated fraction, nano-LC MS equipped with nano-ESI source and consisting of Ultimate HPLC system (LC Packings) and a QSTAR PULSAR I hybrid Q-TOF MS/MS system (Applied Biosytems/PE SCIEX) was used. The QSTAR was operated at resolution of 8000 to 10000 at constant mass for 24 hours. A spray tip was established to a voltage of 2300 V, and all the mass values detected by QSTAR were measured using Analyst QS software supplied by Applied Biosystems Inc. (AB). For MS/MS analysis, common mass values spectra were analyzed by non-redundant database using MASCOT search engine (version 1.7, in-house) to obtain sequence information. The obtained MASCOT results had higher MOWSE values than indicated by random match (p<0.05).

6. Manufacture of Plasmid, Transfection and Purification of Protein

Figure 8:
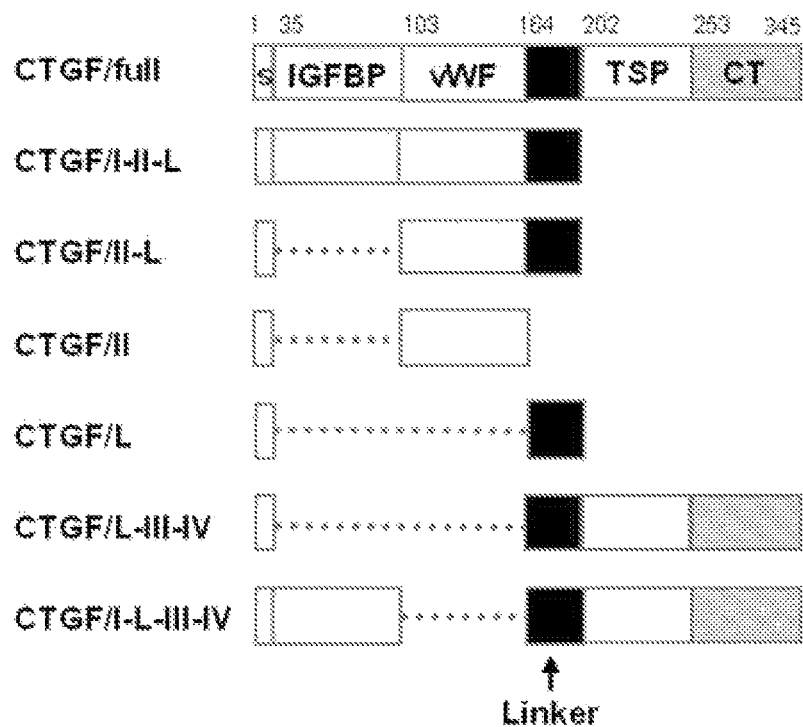
FIG. 8 is a schematic drawing showing a method for determining CTGF binding region to FPRL1.

The full length and deleted variant of Xenopus CTGF inserted into pCS2$^+$ expression vector containing Flag-tag sequence after chordin signal peptide up to Ala41 was supplied from E. M. De Robertis (University of California, Los Angeles, Calif.) (EcoRI-Chordin signal peptide-20 N. terminal AAs of chordin-FLAG epitope (DYKDDDDK)-Xho I-INSERT-Xba I in pCS2$^+$) (Abreu, J. G., Ketpura, N. I., Reversade, B. & De Robertis, E. M. Connective-tissue growth factor (CTGF) modulates cell signalling by BMP and TGF-[beta]. Nat Cell Biol 4, 599-604, 2002). The deleted variant was named as CTGF/I-II-L, CTGF/II-L, CTGF/II, CTGF/L, CTGF/L-III-IV, and CTGF/1-L-III-IV, of which specific deletions are shown in FIG. 8 (The deleted part is indicated by dotted line).

The flag-tagged secretory protein was obtained by transient transfection of HEK 293T cells (ATCC, Manassas, Va., USA) using lipofectamine (Invitrogen, Carlsbad, Calif.) according to manufacturer's instruction. From HEK293T cells, full length and deleted variant Flag-CTGF were affinity-purified using anti-Flag M2 affinity gel column, and Flag peptide was eluted according to manufacturer's instruction. The purity of the protein was determined through silver staining using a Silver Stain Plus kit (Bio-Rad).

7. Biotinylation and Flow Cytometry

To evaluate the degree of binding of linker polypeptide corresponding to the link region of human CTGF, linker polypeptide was labeled using a EZ-Link Micro Sulfo-NHS-LC-Biotinylation kit (Pierce Chemical Co., Rockford, Ill., USA) according to the manufacturer's instruction. The linker polypeptide was cultured at room temperature for 1 hour in PBS with 9 mM sulfo-NHS-LC-biotin (Pierce Chemical Co., Rockford, Ill., USA). During biotinylation, vector/RBL cells, FPR/RBL cells, FPRL1/RBL cells, or HUVECs were treated with trypsin, and collected, and then, treated with rabbit serum at room temperature for 30 minutes. After culturing the biotinylated linker polypeptide in the ice for 30 minutes, the cells were shortly washed with ice-cold PBS, cultured with antihuman fluoroscein-5-isothiocyanate (FITC)-conjugated streptavidin (Pierce Chemical Co.), and then, washed with ice-cold PBS, and fixed with 1% formaldehyde solution. And then, they were analyzed using FACS Caliber system (BD Biosciences, San Jose, Calif.) with CellQuest and WinMDI 2.9 software according to previously known method (He, R., Sang, H. & Ye, R. D. Serum amyloid A induces IL-8 secretion through a G protein-coupled receptor, FPRL1/LXA4R. Blood 101, 1572-1581, 2003).

8. Measurement of $Ca^{2+}$

FPRL1/RBL, vector/RBL or FPR/RBL cells were cultured in a fluo-3-AM working solution containing 0.03% (w/v) plutonic F-127 (Molecular Probes) at 37° C. for 1 hour so that the final concentration of fluo-3-AM became 20 uM/L. After the culturing, fluo-3-AM fluorescence occurred at 488 nm with high-power Ar+ laser in the cells, and the emission band was measured at 530 nm with photomultiplier. Fluorescence signal was detected using confocal laser scanning system (LSM 510 Meta; Carl Zeiss, Jena, Germany) equipped with Nikon E-600 Eclipse microscope. Fluorescence intensities before adding CTGF ($F_0$) and after adding CTGF (F) were measured. Change in the intracelullar $Ca^{2+}$ concentration $[Ca^{2+}]_i$ was indicated by $F/F_0$ ratio. From each cell, 50 to 120 images were scanned.

9. In Vitro Angiogenesis Assay

For proliferation assay, HUVECs were plate cultured in a gelatin-coated 24-well culture dish at $2 \times 10^4$ cells/well and allowed to adhere overnight. 4 hours after serum was depleted, the cells were treated with various mitogen (CTGF linker polypeptide, CTGF) for 48 hours. [$^3$H]-thymidine (1 µCi, Amersham International) was added to each well 6 hours before final culture. The inserted [$^3$H]-thymidine was extracted in 0.2 M NaOH and 0.1% SDS solution at 37° C. for 1 hour. Radioactivity was measured using liquid scintillation counter (Beckmann Instruments), which was repeated three times, and the result was indicated by mean±standard deviation per minute.

The activities of wound migration and tube formation of HUVECs were confirmed as follows.

Specifically, HUVECs inoculated on a 60-mm culture dish to confluence were wounded with the end of a pipette, and treated with linker polypeptide ($10^{-1} \sim 10^2$ nM) or recombinant CTGF (recombinant human CTGF, rhCTGF; BioVendor R&D, NC, USA) ($10^1$ or $10^2$ nM) in Medium 199 to which 1% serum and 1 mM thymidine were added. After culturing 16 hours, the number of cells that migrated over a reference line was counted to quantify the degree of migration, and the cells were photographed with 50× magnification.

Meanwhile, to analyze tube formation, HUVECs were inoculated on the previously polymerized Matrigel (BD Biosciences) layer together with a certain amount of linker polypeptide, rhCTGF or VEGF-$A_{165}$. After culturing for 18 hours, the shape of the cells was observed by phase-contrast microscopy, and photographed with 40× magnification. By measuring the length of tubes 5 times in LPF (low-power fields) randomly selected from each well using image-Pro Plus v4.5 (Media Cybernetics, Silver Spring, Md.), the degree of tube formation was quantified.

10. Analysis of CAM (Chorioallantoic Membrane)

In vivo CAM analysis was conducted according to a previously known method (Lee, M.-S. et al. Angiogenic Activity of Pyruvic Acid in in Vivo and in Vitro Angiogenesis Models. *Cancer Res* 61, 3290-3293, 2001).

Fertilized eggs were cultured in an egg breeder set to fixed moisture at 37° C. 3 days after the culture, to take off expressed CAM from the shell, about 2 ml of egg albumin was taken out with 18-gague subcutaneous needle. After additionally culturing for 6 days, thermanox coverslips (Nunc) containing the sample was dried in the air, and applied to the CAM surface to test the activity of angiogenesis by linker polypeptide or rhCTGF. After 3 days, 1-2 ml of 10% (w/v) Intralipose was injected into chorioallantois, and observed with microscope.

11. Preparation of siRNA to FPRL1 Transcription and Transfection

To inhibit transcription of human FPRL1 using siRNA, siRA to FPRL1 (sense: UUCACAUCGUGGUGGA-CAUdTdT (SEQ ID NO. 3), anti-sense: AUGUCCACCAC-GAUGUGAAdTdT (SEQ ID NO. 4)) was used. As result of BLAST search of the siRNA sequence, it was confirmed that there is no significant similarity to other sequences in the database. The oligonnucleoride showed similar results. HUVECs were used for siRNA transfection. The cells were transfected to the final concentration of 20 nM with FPRL1 siRNA (SEQ ID NO. 3 and SEQ ID NO. 4) or transfected with luciferase siRNA (SEQ ID NO. 11 and SEQ ID NO. 12) as control. At this time, a lipofectamine reagent (Invitrogen Life Technologies) was used according to the manufacturer's instruction. The cells were washed with serum-free medium, and cultured with the transfection mixture to which medium containing 20% (v/v) FBS was added for 4.5 hours. 24 hours and 48 hours after culturing, the cells were collected, and the degree of FPRL1 expression was confirmed by RT-PCR analysis.

12. RT-PCR Analysis

All RNAs were separated from the transfected HUVECs according to the manufacturer's instruction using commercially available TRI reagent (Molecular Research Center). First-strand cDNA was synthesized according to the manufacturer's instruction using 3 ug of each DNA-free total RNA sample and oligo(dT)$_{15}$ and Moloney murine leukemia virus reverse transcriptase (Promega, Wis., USA). And then, with 50 ul of a reaction solution containing 1×PCR buffer, 200 uM dNTPs, 10 uM of each specific primer (sFPRL1: 5'-GACCT-TGGATTCTTGCTCTAGTC-3' (SEQ ID NO. 13), asFPRL1: 5'-GGATCAGTCTCTCTCGGAAGTC-3' (SEQ ID NO. 14), sCTGF: 5'-TTCCAGAGCAGCTGCAAGTACCA-3' (SEQ ID NO. 15), asCTGF: 5'-TTGTCATTGGTAAC-CCGGGTGGA-3' (SEQ ID NO. 16)), and 1.25 units Taq DNA polymerase (Perkin-Elmer), the same amount of cDNA was amplified. The amplification product was electrophoresed on 1.5% agarose gel, stained with EtBr (ethidium bromide) and developed by infrared penetration.

<Experiment Results>

1. ERK Phosphorylation Inducing Activity of Conditioned Medium of HUVECs Treated with VEGF-A Vascular endothelial growth factor-A (VEGF-A), which is a kind of inflammatory cytokine, shares a lot of cellular functions with G-protein-coupled receptor FPRL1 (formyl peptide receptor-like 1) for the control of angiogenesis. However, it is unknown how VEGF-A and FPRL1 interacts.

To confirm this, the inventors obtained conditioned medium (CM) in HUVEC treated with VEGF-A, and FPRL1-overexpressing cells FPRL1/RBL were treated therewith in the concentration of 10 ng/ml or 50 ng/ml for 8 hours. At this time, as positive control, FPRL1 agonistic peptide WKYMVm (Trp-Lys-Tyr-Met-Val-D-Met, SEQ ID NO. 1) was treated with 10 nM.

After the treatment, immunoblot was conducted on cell lysate that was transferred to a nitrocellulose film with anti-phospho ERK (extracellular signal regulated kinase)1/2 and anti-ERK1/2 antibody (Cell Signaling Technology, Beverly, Mass., USA), and then, the film was visualized with a chemiluminescence substrate (Amersham Pharmacia), and the results are shown in FIG. 1.

As shown in FIG. 1, it can be seen that the conditioned medium obtained in HUVECs treated with VEGF-A increased ERK phosphorylation in a concentration-dependent manner.

Meanwhile, the above described vector/RBL, FPR/RBL, or FPRL1/RBL cells were respectively treated with the above conditioned medium or VEGF-A at the concentration of 10 ng/ml for 8 hours, and positive control was treated with 10 nM of agonistic peptide WKYMVm (SEQ ID NO. 1). And then, immunoblot was conducted as described above, and the results are shown in FIG. 2.

Figure 2:
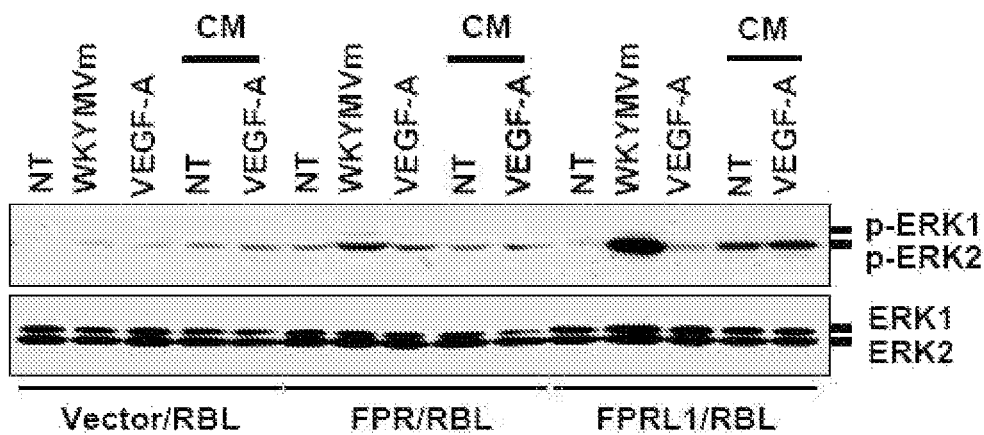
FIG. 2 shows the experiment results confirming that conditioned medium, VEGF-A and positive control (WKYMVm) induce ERK phosphorylation only in FPRL1-overexpressing FPRL1/RBL cells.

As shown in FIG. 2, it can be seen that conditioned medium, VEGF-A and positive control all increased ERK phosphorylation only in EPRL1-overexpressing FPRL1/RBL cells. Thus, it can be seen that ERK phosphorylation induced by the conditioned medium is specific to FPRL1.

2. Identification of Protein Having Erk Phosphorylation Inducing Activity in Conditioned Medium As described in the <Experiment method 5>, FPRL1/RBL cells were treated with 40 ug of the HPLC fraction of the conditioned medium for 5 minutes, and the result confirming whether ERK phosphorylation occurred as described in the <Experiment result 1> was shown in FIG. 3.

Figure 3:
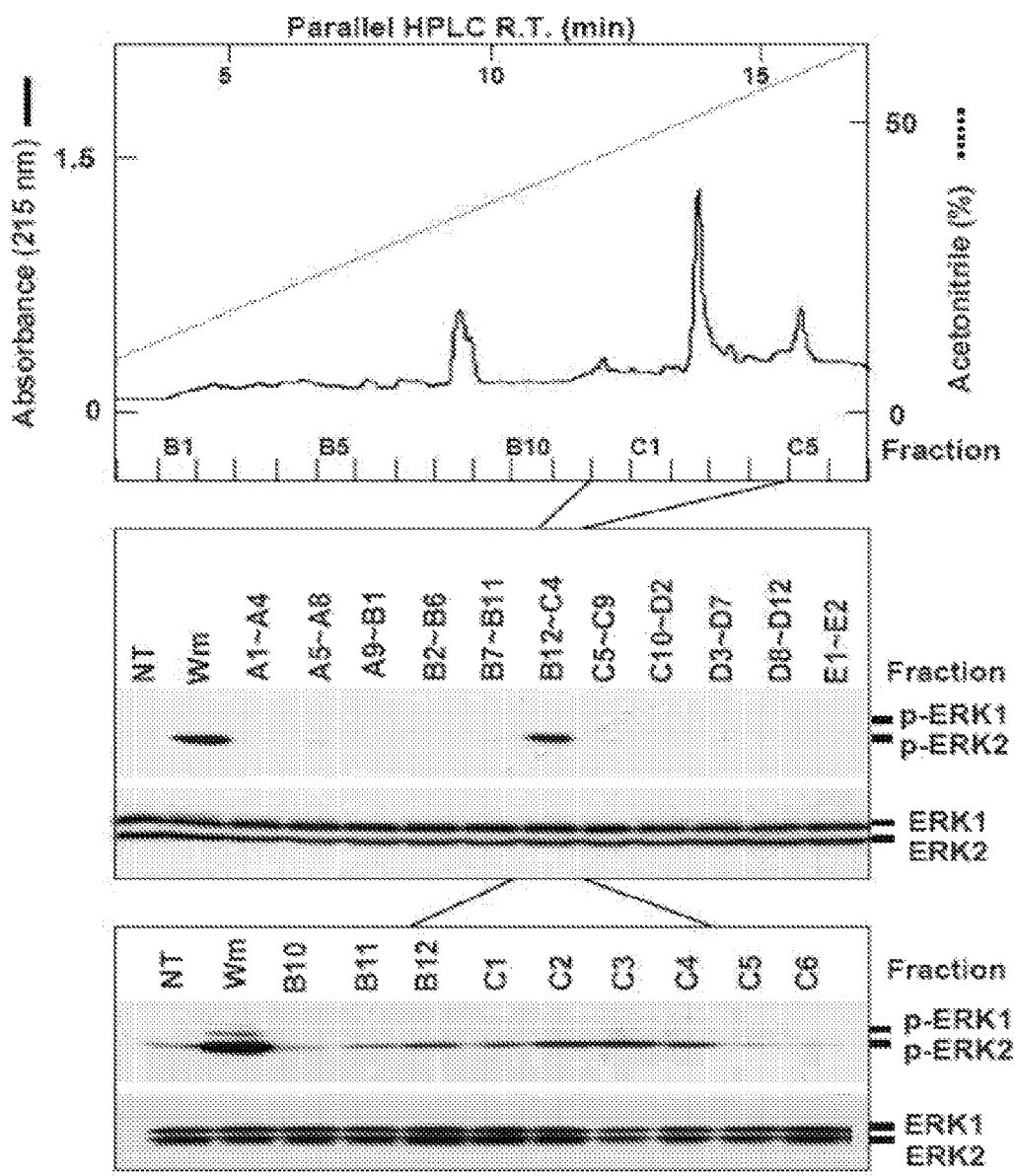
FIG. 3 shows the results of confirming whether ERK phosphorylation occurs by treating FPRL1/RBL cells with HPLC fraction of conditioned medium.

As shown in FIG. 3, it can be seen that fractions containing B12 to C4 induce ERK phosphorylation in FPRL1/RBL cells, and as result of examining the active peak of each fraction of B11 to C4, it can be seen that peaks are observed only in B12, C3 fractions.

From the results, it was assumed that the protein having activity of inducing ERK phosphorylation in FPRL1/RBL cells is contained in B12, MS/MS analysis as described in the <Experiment method 5> was conducted on the B12 fraction, and the results are shown in FIG. 4.

As shown in FIG. 4, 5 polypeptide sequences (underlined parts in FIG. 4) corresponding to the amino acid sequence of human connective-tissue growth factor (CTGF) were detected.

Therefore, it can be seen that protein having activity of inducing ERK phosphorylation in FPRL1/RBL cells is CTFG.

3. CTGF Expression Induction by VEGF-A

From the <Experiment 2>, it was considered that in the conditioned medium secreted in HUVECs treated with VEGF-A, CTGF may bind to FPRL1 to induce ERK phosphorylation in FPRL1/RBL cells.

To confirm this, RT-PCR and Western Blot analysis were conducted as described in the Experiment method. Specifically, the results of analyzing the degree of CTGF expression in cell lysate or conditioned medium of HUVECs treated with VEGF-A according to treatment time and treatment amount of VEGF-A were respectively shown in FIG. 5 and FIG. 6.

As shown in FIG. 5, as result of RT-PCR analysis, it can be seen that CTGF mRNA increases from the time when 0.5 hours have elapsed after treating HUVECs with VEGF-A, and as result of Western blot analysis, it can be seen that CTGF value increases from the time when 2 hours have elapsed in the cell lysate, and that CTGF value increases from the time when 4 hours have elapsed in the conditioned medium.

Figure 6:
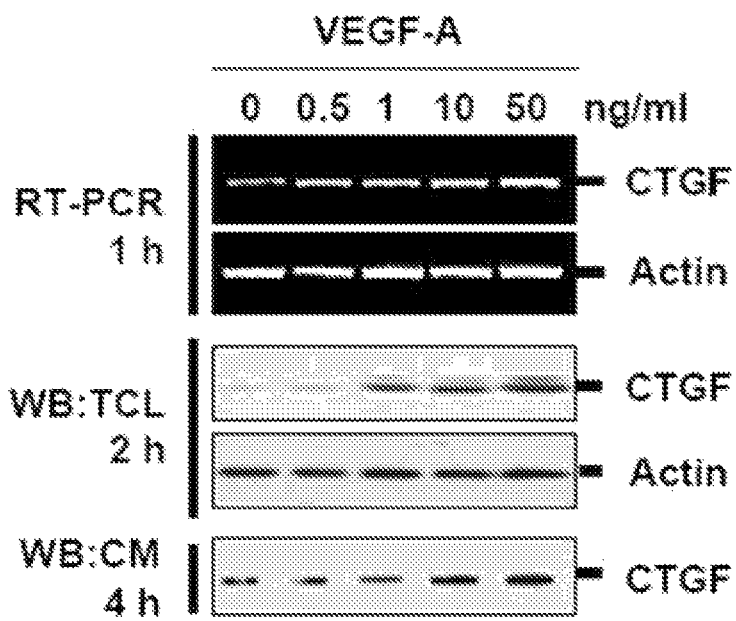
FIG. 6 shows the results of analyzing the degree of CTGF expression in cell lysate or conditioned medium of HUVECs treated with VEGF-A according to treatment amount of VEGF-A.

And, as shown in FIG. 6, as results of RT-PCR and Western blot analysis, it can be seen that CTGF value increases in proportion to the treatment amount of VEGF-A.

Meanwhile, the inventors additionally confirmed whether VEGF-A receptor is involved in CTGF synthesis. Specifically, HUVECs were treated with neutralizing antibodies to VEGF-A (R&D Systems, Minneapolis, Minn., USA), VEGF receptor-1 (VEGFR-1) (R&D Systems, Minneapolis, Minn., USA) and VEGF receptor-2 (VEGFR-2) (R&D Systems, Minneapolis, Minn., USA), and as control, treated with IgG antibody at the concentration of 5 ug/ml for 30 minutes, and they were treated with VEGF-A at the concentration of 20 ng/ml. After 2 hours have elapsed, cell lysate was obtained and immunoblot was conducted with anti-human CTGF, and the result is shown in FIG. 7.

Figure 7:
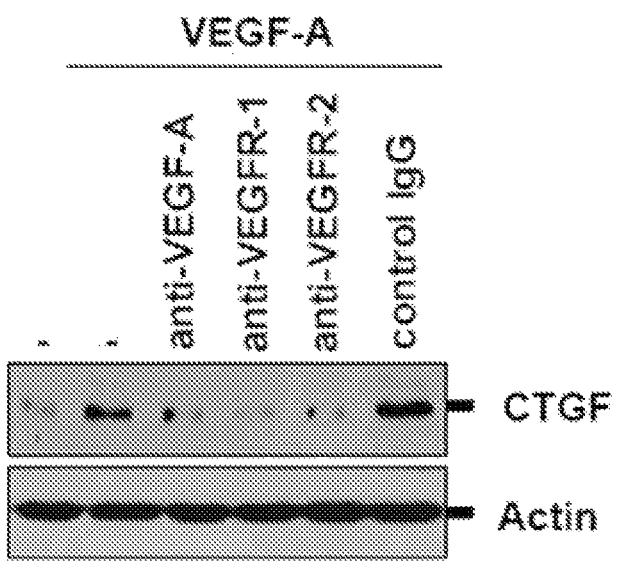
FIG. 7 shows the results confirming that CTGF expression is significantly decreased when antibody to VEGF-A receptor is administered.

As shown in FIG. 7, it can be seen that if antibody to VEGF-A receptor is administered, CTGF expression is remarkably decreased. Thus, it can be seen that CTGF expression induction of VEGF-A is controlled by receptor coupling.

4. Determination of CTGF Binding Site to FPRL1

To determine CTGF binding site to FPRL1, plasmids in which gene encoding full length CTGF protein or partly deleted protein CTGF/I-II-L, CTGF/II-L, CTGF/II, CTGF/L, CTGF/L-III-IV, and CTGF/1-L-III-IV are inserted were prepared as shown in FIG. 8 according to the method described in the <Experiment method 6>, and transfected into HEK 293T cells (ATCC, Manassas, Va., USA), and each protein was purified.

Figure 9:
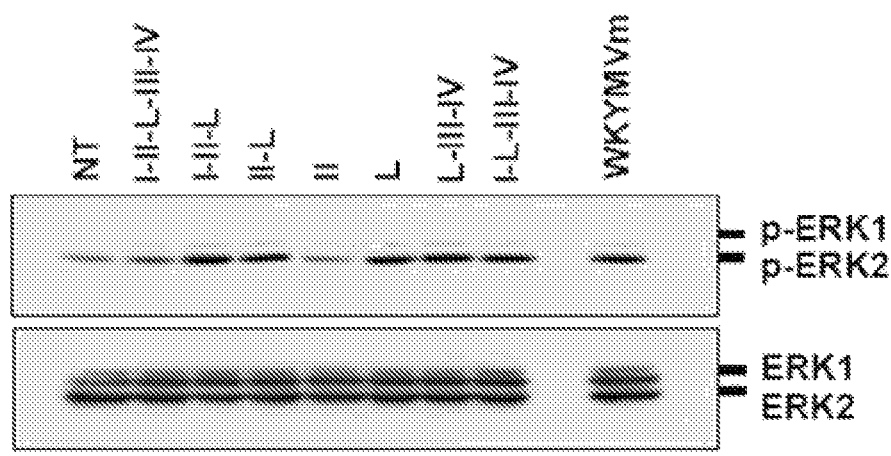
FIG. 9 shows the results confirming whether full length CTGF protein or partly deleted protein thereof induces ERK phosphorylation in FPRL1/RBL cells.

To confirm whether the purified proteins induce ERK phosphorylation in FPRL1/RBL cells, immunoblot was conducted as described in the <Experiment result 1>, and the results are shown in FIG. 9.

As shown in FIG. 9, it can be seen that all proteins except CTGF/II induce ERK phosphorylation. By drawing common region of deleted proteins except CTGF/II from the results, it can be seen that $164^{th}$ to $201^{st}$ (indicated by bold letter, SEQ ID NO. 5) of full length CTGF protein (MTAASMGPVR-VAFVVLLALCSRPAVGQNCSGPCRCPDE-PAPRCPAGVSLVLDGC GCCRVCAKQLGELCTERD-PCDPHKGLFCDFGSPANRKIGVCTAKDGAPCIFGGTV YRSGESFQSSCKYQCTCLDGAVGCM-PLCSMDVRLPSPDCPFPRRVKLPGKCCEEW VCDEP-KDQTVVGPALAAYRLEDTFGPDPT-MIRANCLVQTTEWSACSKTCGMGIST RVTNDNASCRLEKQSRLCMVR-PCEADLEENIKKGKKCIRTPKISKPIKFELSGCTSM KTYRAKFCGVCTDGRCCTPHRTT-TLPVEFKCPDGEVMKKNMMFIKTCACHYNCP GDN-DIFESLYYRKMYGDMA) is CTGF binding site to FPRL1.

5. Confirmation of FPRL1 Binding of CTGF Linker Polypeptide 10 nM of linker polypeptide (SEQ ID NO. 6, EWVCDEP-KDQTVVGPALAAYRLEDTFGPDPTMIRANCLV, further containing one amino acid (E) at N-terminal of SEQ ID NO. 5) including the CTGF binding region confirmed in the <Experiment result 4> was biontinylated as described in the <Experiment method 7>, and it was cultured with FPRL1/RBL, vector/RBL or FPR/RBL cells, and then, flow cytometry was conducted and the results are shown in FIG. 10.

Figure 10:
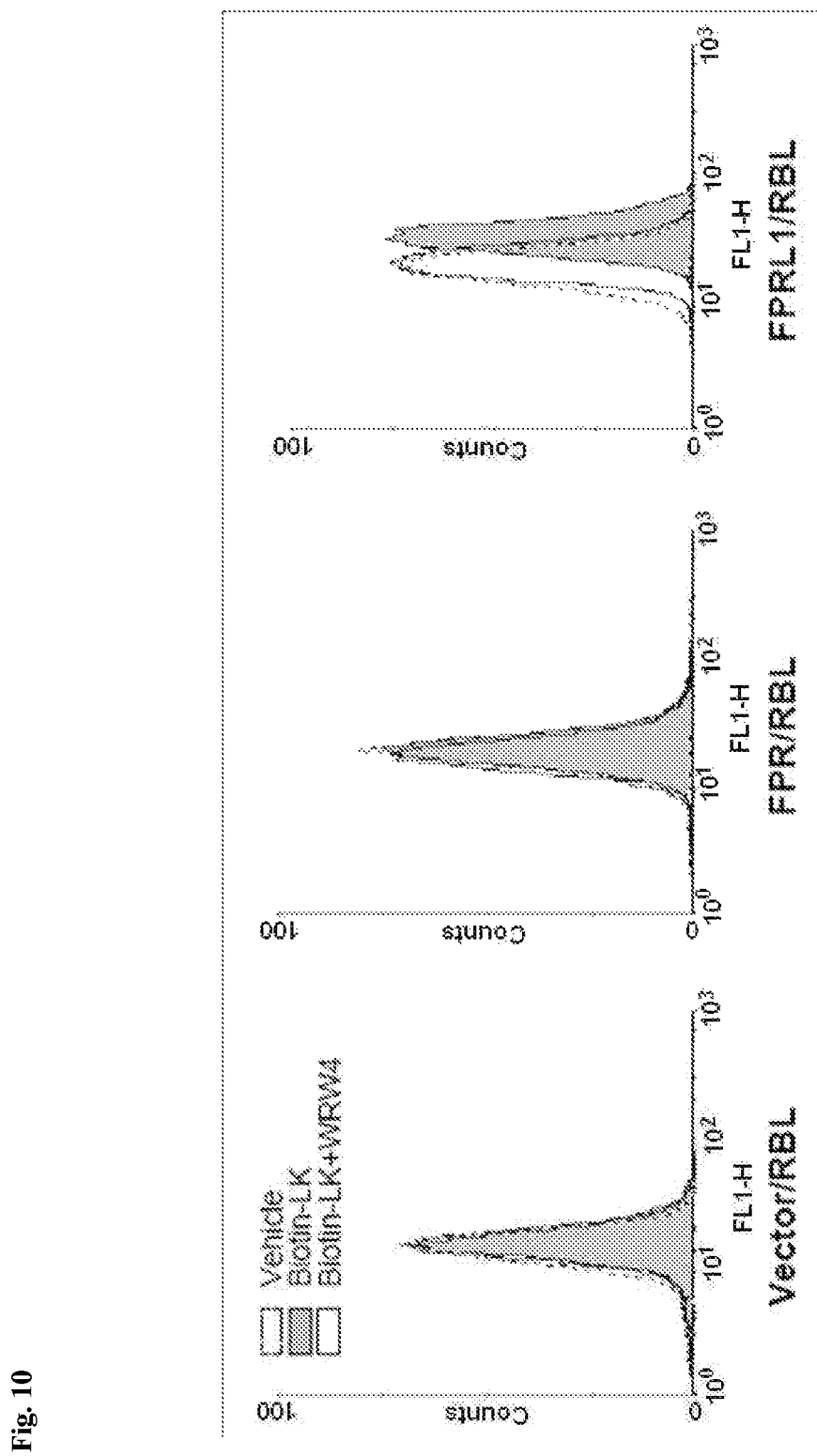
FIG. 10 shows the results confirming whether CTGF linker polypeptide of SEQ ID NO. 6 binds only to FPRL1/RBL cells.

As shown in FIG. 10, it can be seen that the CTGF linker polypeptide binds only to FPRL1/RBL cells. And, as shown in FIG. 1, it can be seen that if FPRL1/RBL, vector/RBL or FPR/RBL cells are treated with 10 uM of FPRL1 antagonist WRW4 (SEQ ID NO. 2) and cultured for 30 minutes, the linker polypeptide binding is inhibited in FPR/RBL cells.

Therefore, from the results, it can be seen that CTGF linker polypeptide specifically binds to FPRL1, and thereby, the linker polypeptide may increase ERK phosphorylation or $Ca^{2+}$ concentration by FPRL1.

6. ERK Phosphorylation Promotion of CTGF Linker Polypeptide

ERK phosphorylation induction of CTGF linker polypeptide was compared to recombinant human CTGF (rhCTGF). Specifically, FPRL1/RBL cells were treated with CTGF linker polypeptide and rhCTGF for 5 minutes at various concentrations, ERK phosphorylation was measured, and the results are shown in FIG. 11.

Figure 11:
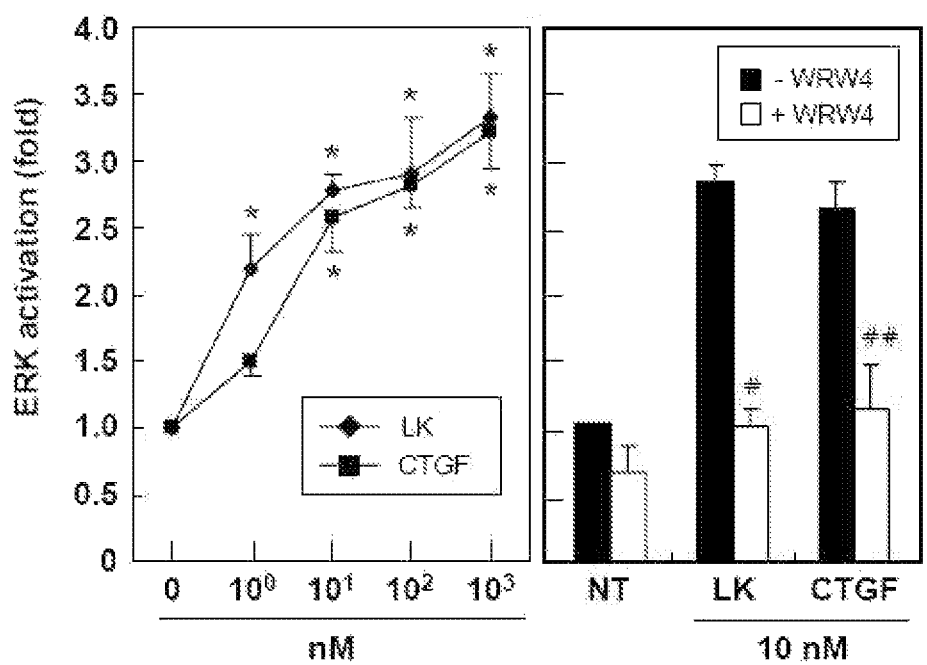
FIG. 11 shows the results confirming that CTGF linker polypeptide of SEQ ID NO. 6 induces ERK phosphorylation to a similar level to rhCTGF, and the ERK phosphorylation is decreased by FPRL1 antagonist (WRW4).

As shown in FIG. 11, it can be seen that CTGF linker polypeptide induces ERK phosphorylation to a similar level to rhCTGF.

And, when 10 nM of the CTGF linker polypeptide or rhCTGF was added to FPRL1/RBL cells, 10 uM of WRW4 was added or not added, and the ERK phosphorylation degrees were compared and the results are shown in FIG. 11.

As shown in FIG. 11, it can be seen that CTGF linker polypeptide (indicated by LK) induces ERK phosphorylation to a similar level to rhCTGF (indicated by CTGF), and particularly, in case FPRL1 antagonist WRW4 is added, ERK phosphorylation is inhibited.

7. $Ca^{2+}$ Concentration Increase by CTGF Linker Polypeptide

Figure 12:
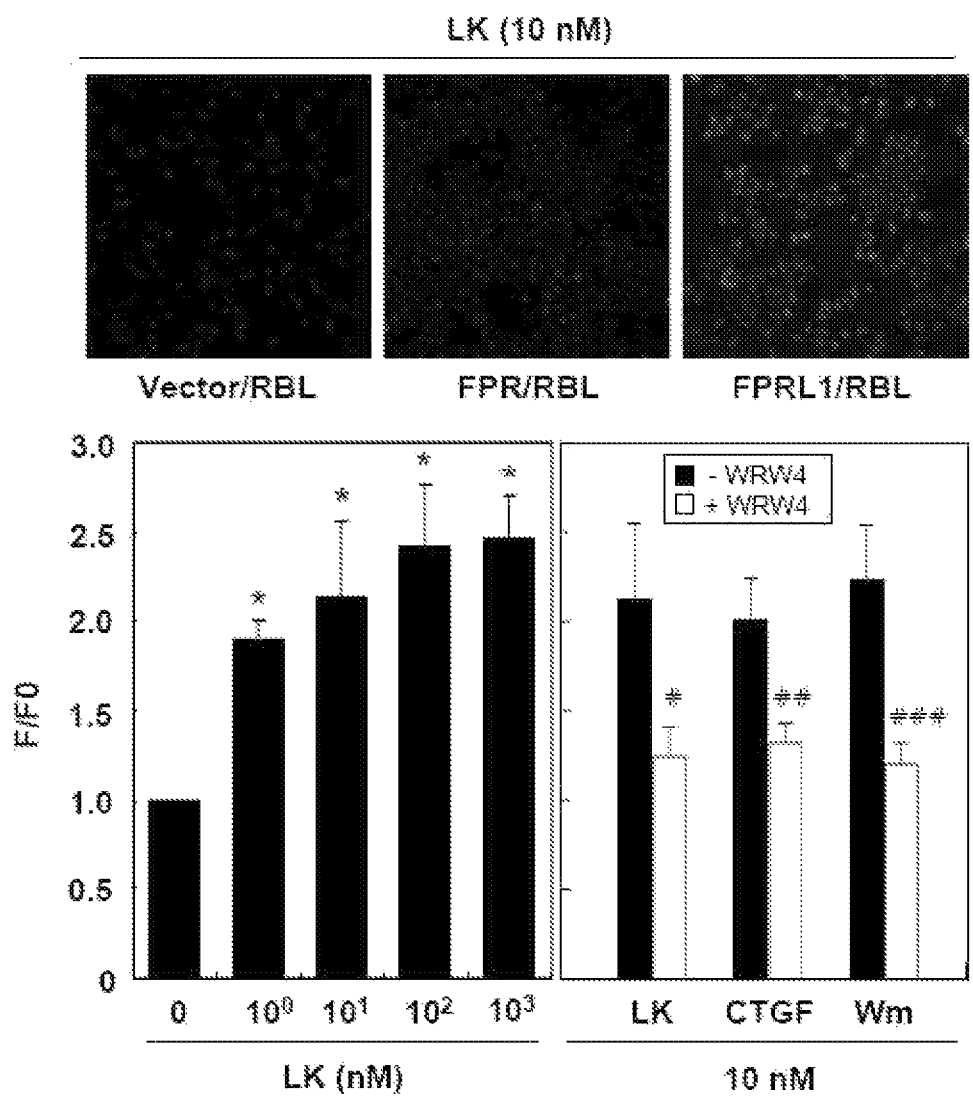
FIG. 12 shows the result confirming whether $Ca^{2+}$ concentration is increased in FPRL1/RBL cells treated with CTGF linker polypeptide of SEQ ID NO. 6.

Since activation of FPRL1 increases intracellular $Ca^{2+}$ concentration, the inventors confirmed whether CTGF linker polypeptide activates FPRL1 to finally increase intracellular $Ca^{2+}$ concentration by the <Experiment method 8>, and the results are shown in FIG. 12.

As shown in FIG. 12, as a result of examining with confocal microscope, $Ca^{2+}$ concentration is increased only in FPRL1/RBL cells treated with CTGF linker polypeptide. Furthermore, as a result of measuring $Ca^{2+}$ concentration in FPRL1/RBL cells, it can be seen that the $Ca^{2+}$ concentration increases dependently upon the concentration of CTGF linker polypeptide, and that the activity is more effective than rhCTGF and is similar to positive control of FPRL1 agonist WKYMVm (indicated by Wm). Also, it can be seen that if FPRL1 antagonist WRW4 10 uM is administered, the degree of intracellular $Ca^{2+}$ concentration increase by CTGF linker polypeptide decreases.

From the results, it can be seen that CTGF directly binds to FPRL1 through the linker region, and thereby, activates FPRL1.

8. Confirmation of Binding to FPRL1 and Activation of CTGF Linker Polypeptide in HUVECs Since FPRL1 is expressed in large quantities in HUVECs, it was confirmed whether CTGF is secreted in HUVECs treated with VEGF-A, and thereby, angiogenesis was examined.

Figure 13:
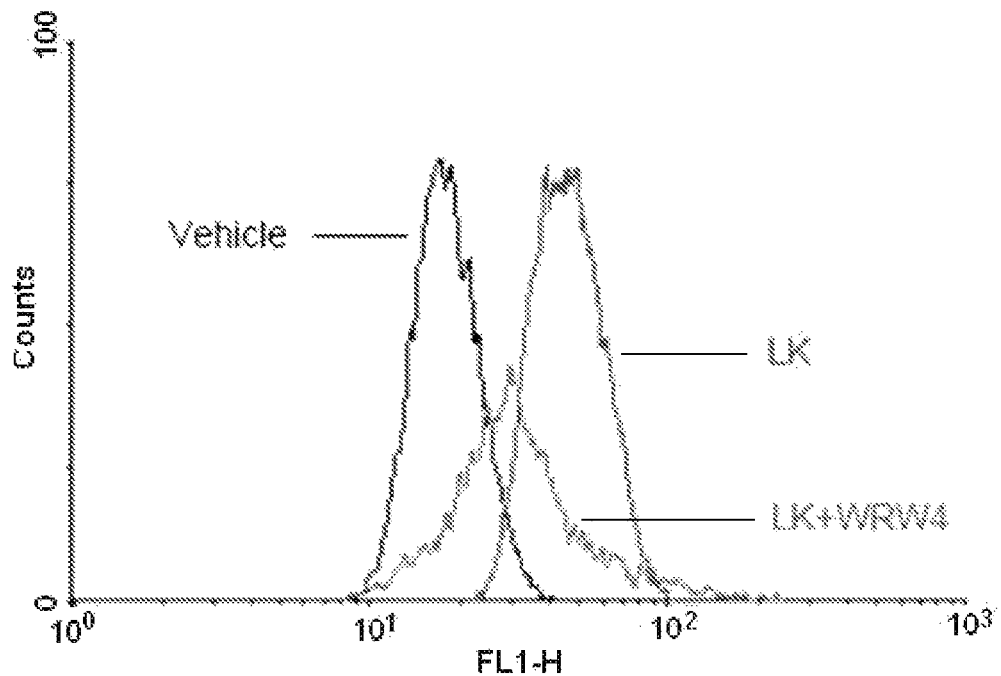
FIG. 13 shows the result confirming whether CTGF linker polypeptide of SEQ ID NO. 6 binds to FPRL1 in HUVECs cells.

It was examined whether the CTGF linker polypeptide binds to FPRL1 in HUVECs as described in the <Experiment method 7>, and the results are shown in FIG. 13. Specifically, HUVECs were treated with 10 nM of the CTGF linker polypeptide, and cultured for 30 minutes, and then, flow cytometry was conducted as described in the <Experiment method 7>. At this time, the cells were treated with 10 uM OF WRW4 together.

As shown in FIG. 13, it can be seen that in case HUVECs were treated with the CTGF linker polypeptide, average value shifts right compared to the case where they were not treated with the CTGF linker polypeptide (treated only with vehicle). However, in case they were treated with FPRL1 antagonist WRW4, the shift is not observed.

Figure 14:
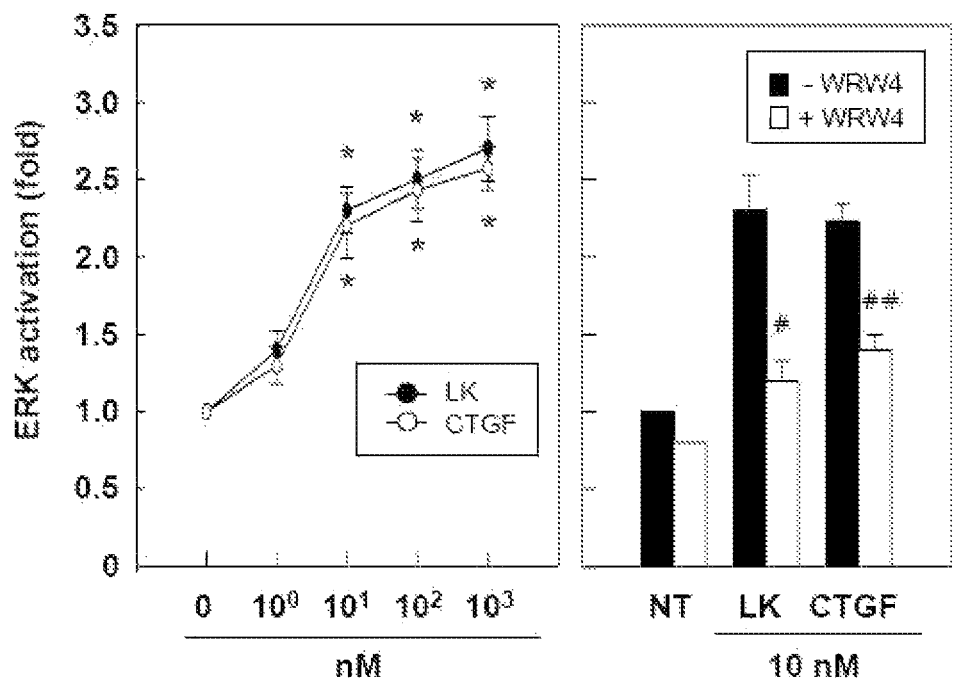
FIG. 14 shows the result confirming that if HUVECs is treated with CTGF linker polypeptide of SEQ ID NO. 6, ERK phosphorylation is effectively induced.

Meanwhile, HUVECs were treated with the CTGF linker polypeptide or rhCTGF at various concentrations for 5 minutes, cell lysate was obtained, and then, immuboblot was conducted with anti-phospho ERK1/2 antibody, and the results are shown in FIG. 14.

As shown in FIG. 14, it can be seen that in case HUVECs is treated with CTGF linker polypeptide, ERK phosphorylation is effectively induced, and that if treated with FPRL1 antagonist WRW4 (10 uM), ERK phosphorylation is inhibited.

Figure 15:
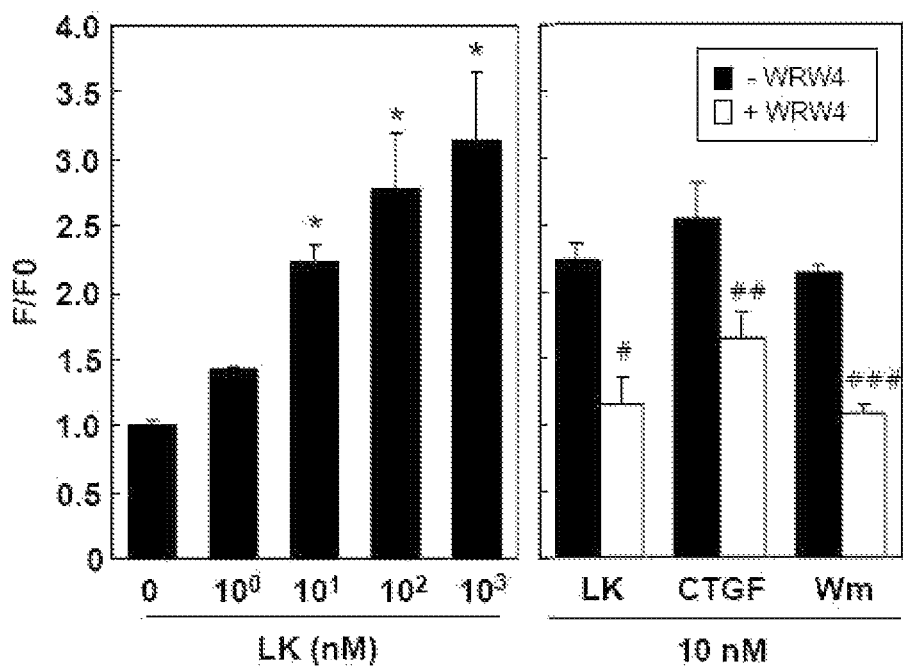
FIG. 15 shows the result confirming that if HUVECs is treated with CTGF linker polypeptide of SEQ ID NO. 6, intracellular $Ca^{2+}$ concentration is increased in a concentration-dependent manner.

And, HUVECs were treated with the CTGF linker polypeptide or rhCTGF at various concentrations for 1 hour, it was confirmed whether intracellular $Ca^{2+}$ concentration increases by the above method, and the results are shown in FIG. 15.

As shown in FIG. 15, it can be seen that although CTGF linker polypeptide increases intracellular $Ca^{2+}$ concentration in a concentration-dependent manner, that's not the case when the cells are treated with FPRL1 antagonist WRW4 (10 uM), From the results, it can be seen that CTGF specifically binds to FPRL1 in HUVECs through the linker region to activate HUVECs.

9. Angiogenesis Inducing Effect of CTGF Linker Polypeptide

If angiogenesis is progressed, endothelial cells grow, the existing blood vessel migrates according to germination, and tube is formed (Carmeliet, P. & Jain, R. K. Angiogenesis in cancer and other diseases. Nature 407, 249-257, 2000), and thus, it was confirmed whether CTGF linker polypeptide induces the angiogenesis by the <Experiment method 9>, and the results are shown in FIGS. 16 to 18.

Figure 16:
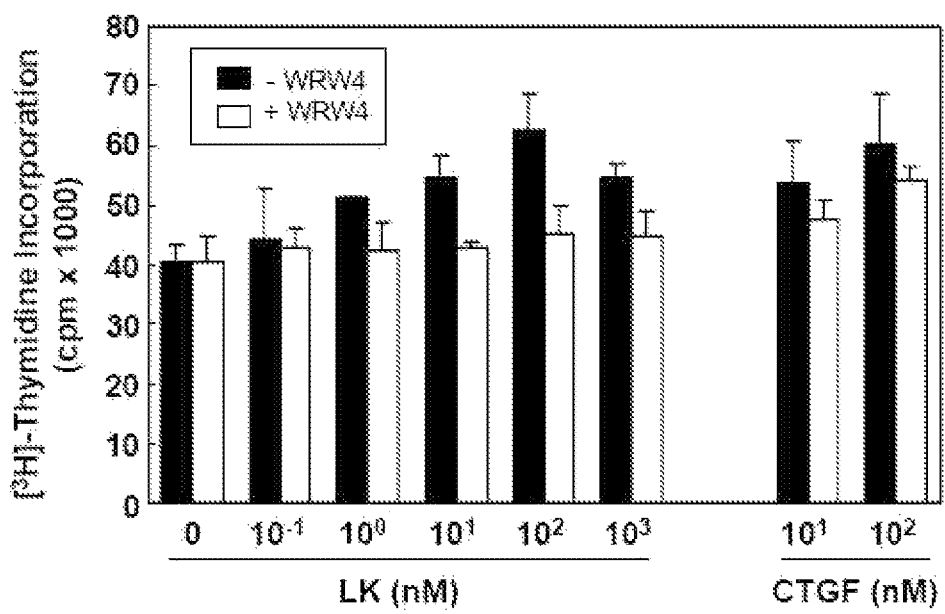
FIG. 16 shows the result confirming that CTGF linker polypeptide of SEQ ID NO. 6 does not significantly influence on the proliferation of HUVECs.

As shown in FIG. 16, although CTGF linker polypeptide induces proliferation of HUVECs in a concentration-dependent manner, the degree is not statistically significant.

Figure 17:
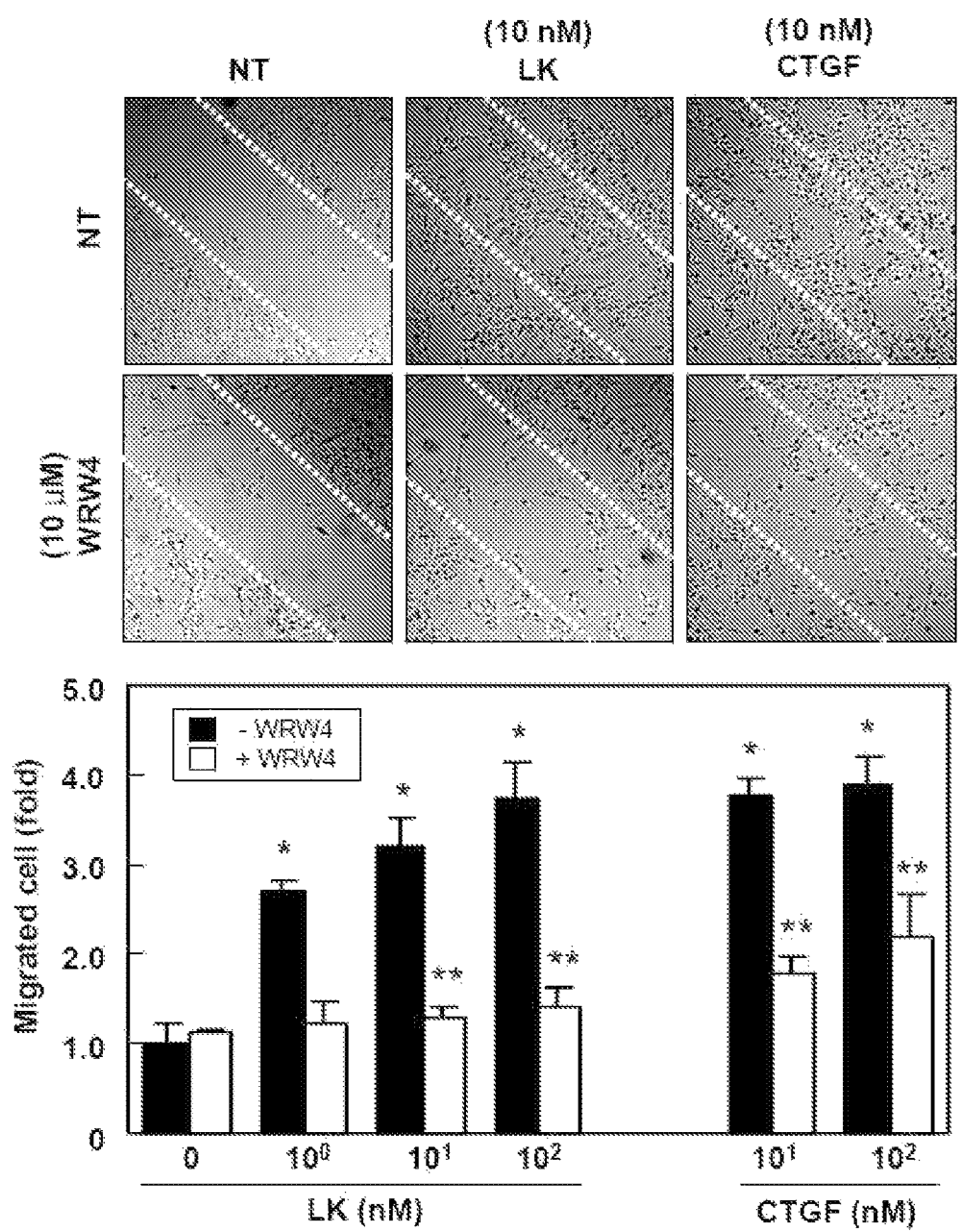
FIG. 17 shows the result confirming that CTGF linker polypeptide of SEQ ID NO. 6 induces migration of HUVECs in a concentration-dependent manner.

And, as shown in FIG. 17, it can be seen that the CTGF linker polypeptide induces migration of HUVECs in a concentration-dependent manner more effectively than recombinant CTGF, and furthermore, it can be seen that in case the cells are treated with FPRL1 antagonist WRW4 (10 uM), the cell migration is not induced.

Figure 18:
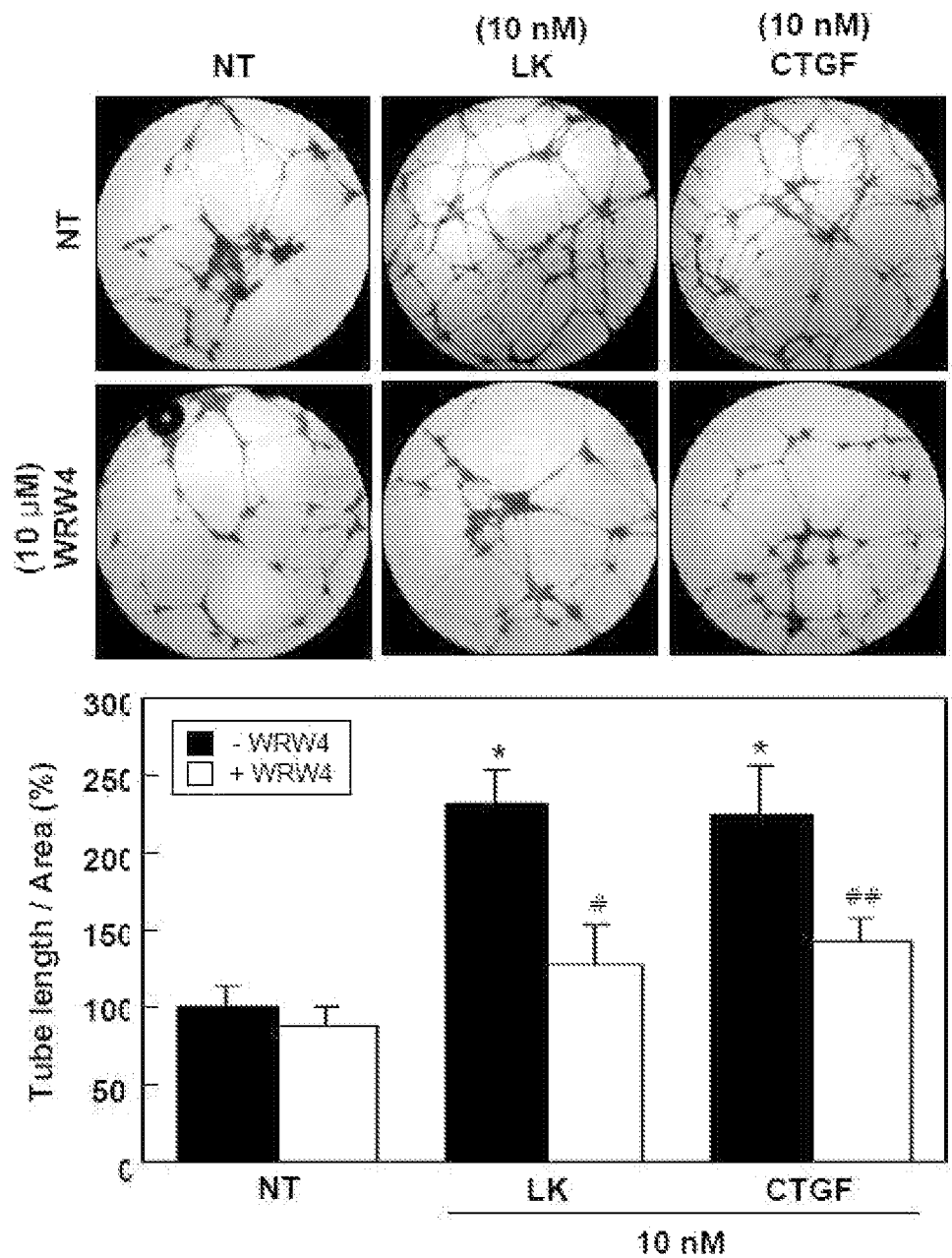
FIG. 18 shows the result confirming that that CTGF linker polypeptide of SEQ ID NO. 6 induces tube formation of HUVECs in a concentration-dependent manner.

And, as shown in FIG. 18, it can be seen that CTGF linker polypeptide induces tube formation of HUVECs more effectively than recombinant CTGF, and furthermore, it can be seen that in case the cells are treated with FPRL1 antagonist WRW4 (10 uM), the tube formation is not be induced.

From the results, it can be seen that since CTGF linker polypeptide induces cell migration and tube formation rather than cell proliferation more effectively than full length CTGF, it may promote angiogenesis.

Figure 19:
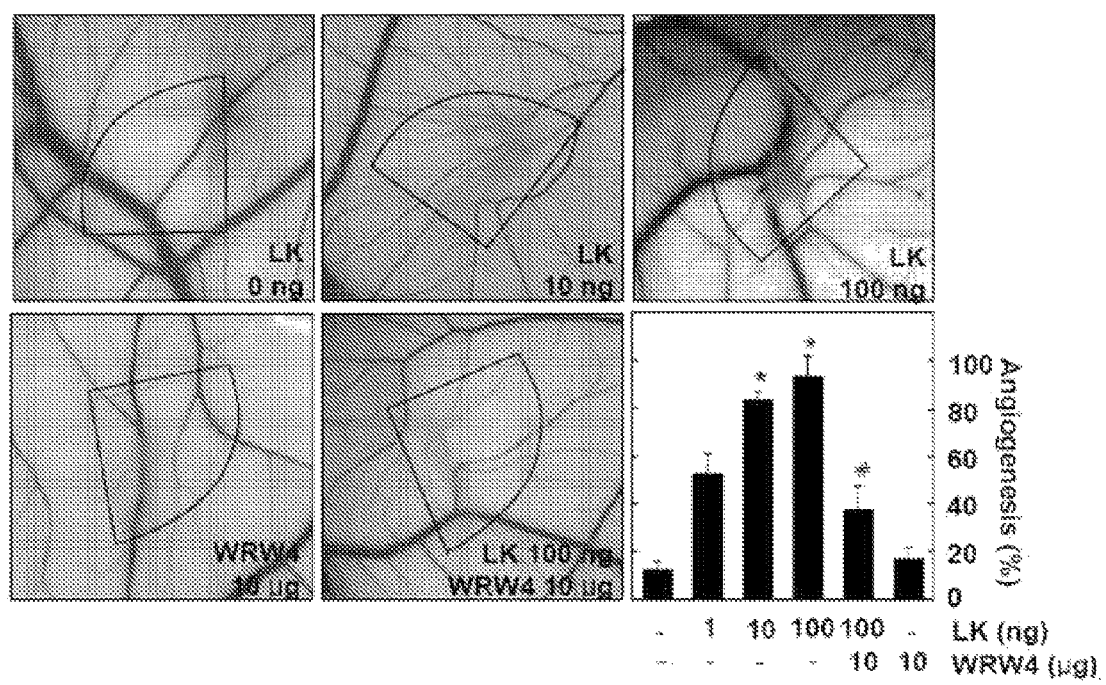
FIG. 19 shows the result confirming that CTGF linker polypeptide of SEQ ID NO. 6 in vivo induces angiogenesis in a concentration-dependent manner.

Thus, based on the results, the inventors confirmed in vivo angiogenesis activity by the <Experiment method 10>, and the results are shown in FIG. 19.

As shown in FIG. 19, it can be seen that CTGF linker polypeptide very strongly induces angiogenesis also in vivo in a concentration-dependent manner, and thus, so called wheel-shaped blood vessel is formed. However, it can be seen that in case the cells are treated with FPRL1 antagonist WRW4 (10 uM), the blood vessel formation is not induced.

Therefore, it can be seen that CTGF binds to FPRL1 through the linker region, and thereby, induce angiogenesis in vitro and in vivo.

10. FPRL1 Expression Promoting Effect of VEGF-A

Based on the results, it was considered that CTGF/FPRL1 assembly may mediate the activity of VEGF-A in the process of angiogenesis.

Figure 20:
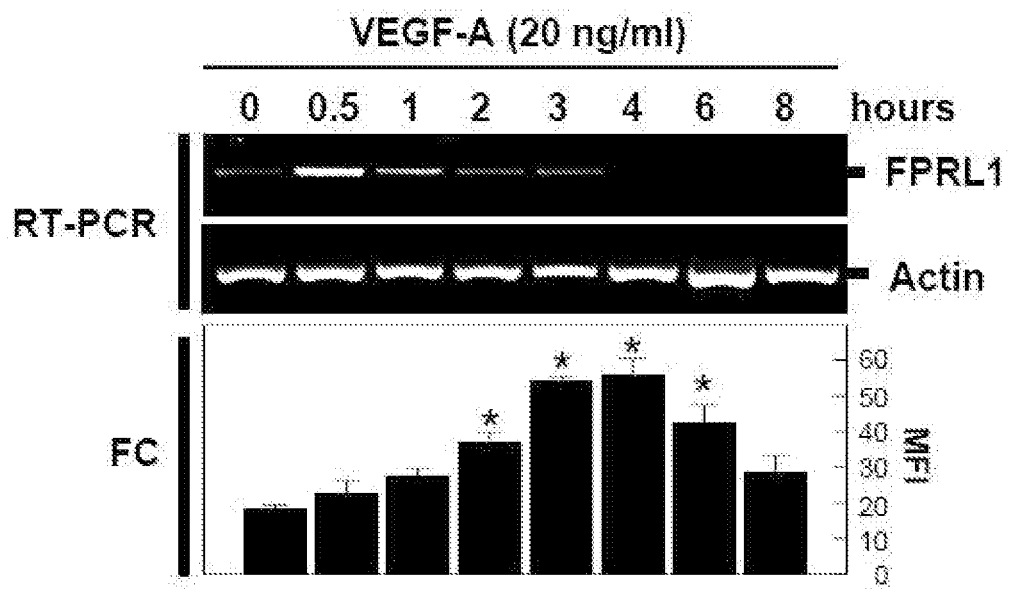
FIG. 20 shows the result confirming whether VEGF-A induces FPRL1 expression in HUVECs cells by conducting RT-PCR or flow cytometry according to incubation time.

Thus, it was confirmed whether VEGF-A induces FPRL1 expression in HUVECs. Specifically, HUVECs were treated with 20 ng/ml of VEGF-A, and cultured for various times, and then, RT-PCR was conducted according to the <Experiment method 12>, the degree of FPRL1 expression was measured, and the results are shown in FIG. 20. And, flow cytometry analysis was conducted according to the <Experiment method 7>, and the results are shown in FIG. 20.

Figure 21:
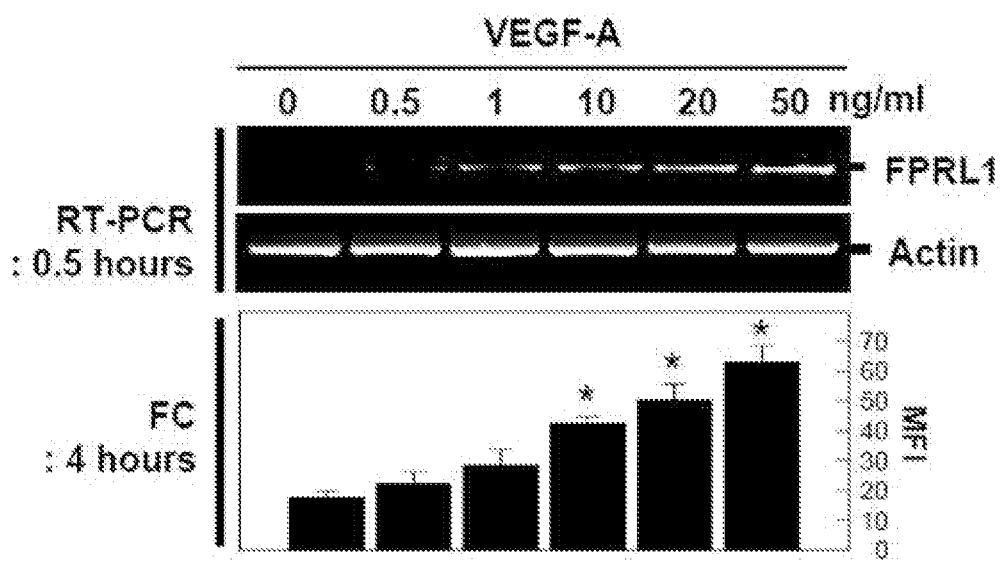
FIG. 21 shows the result confirming whether VEGF-A induces FPRL1 expression in HUVECs cells by conducting RT-PCR or flow cytometry according to treatment amount.

And, HUVECs were treated with various concentrations of VEGF-A and cultured, and then, RT-PCR was conducted according to the <Experiment method 12>, the degree of FPRL1 expression was measured, and the results are shown in FIG. 21. And, flow cytometry analysis was conducted according to the <Experiment method 7>, and the results are shown in FIG. 21.

As shown in FIGS. 20 and 21, it can be seen that VEGF-A induces expression of FPRL1 in a concentration-dependent manner.

11. Angiogenesis Inducing Effect of VEGF-A Through CTGF/FPRL1 Assembly

It was additionally confirmed whether FPRL1 antagonist WRW4 inhibits angiogenesis induced by VEGF-A. Thereby, it can be seen that FPRL1 activation is involved in the angiogenesis induced by VEGF-A.

Figure 22:
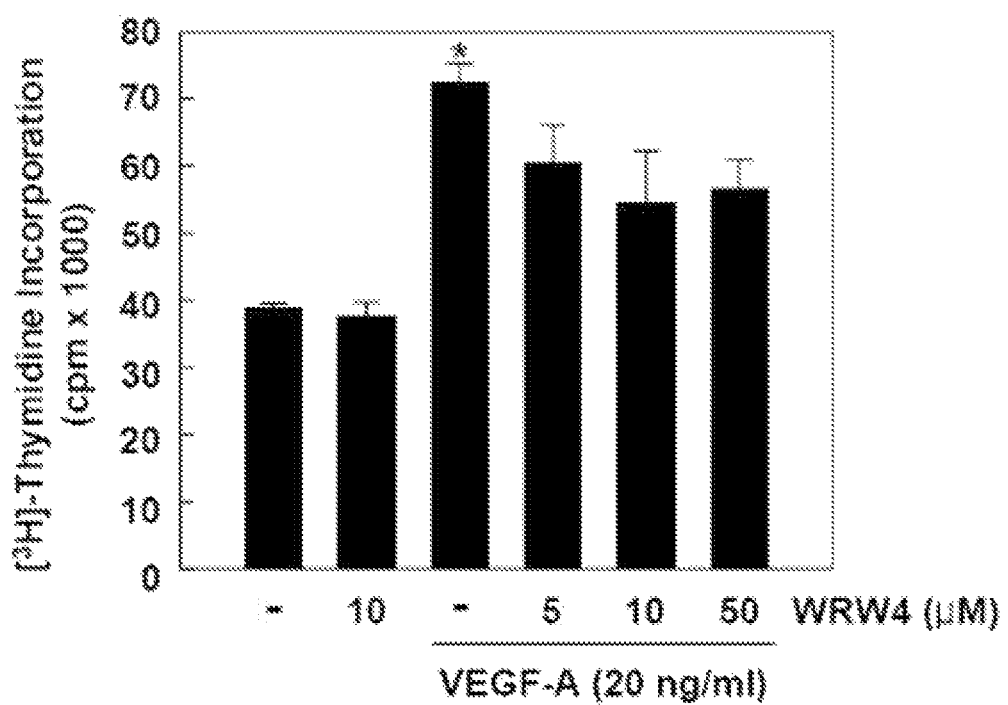
FIG. 22 shows the experiment result confirming that the proliferation of HUVECs induced by VEGF-A is not significantly decreased by FPRL1 antagonist (WRW4).
Figure 23:
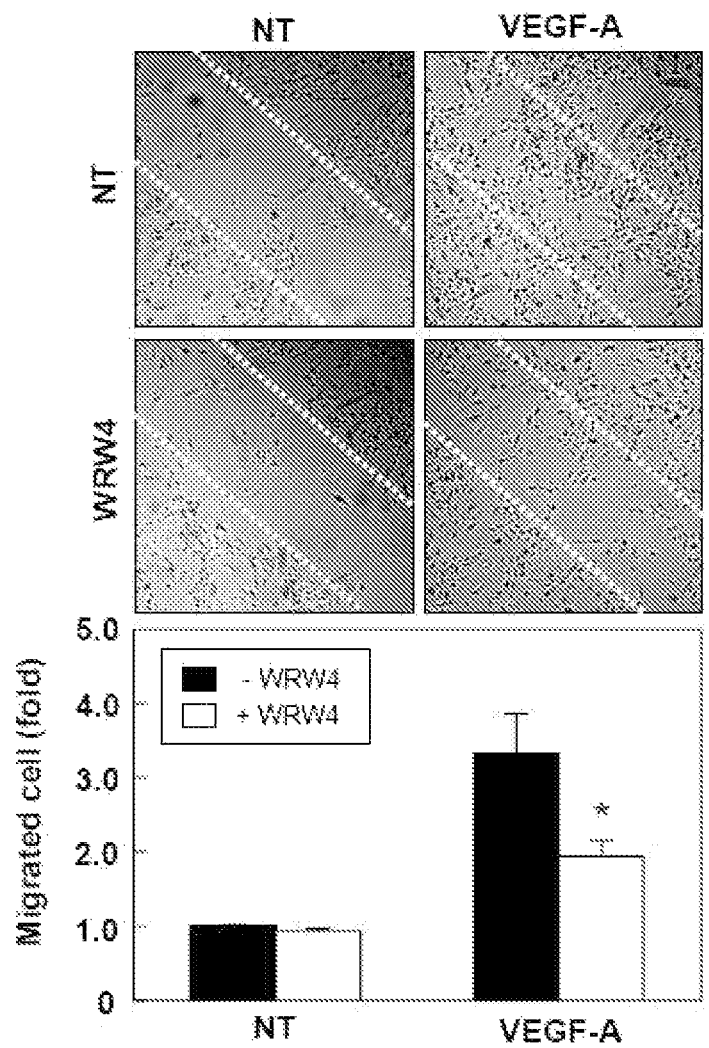
FIG. 23 shows the experiment result confirming that migration of HUVECs induced by VEGF-A is significantly decreased by FPRL1 antagonist (WRW4).
Figure 24:
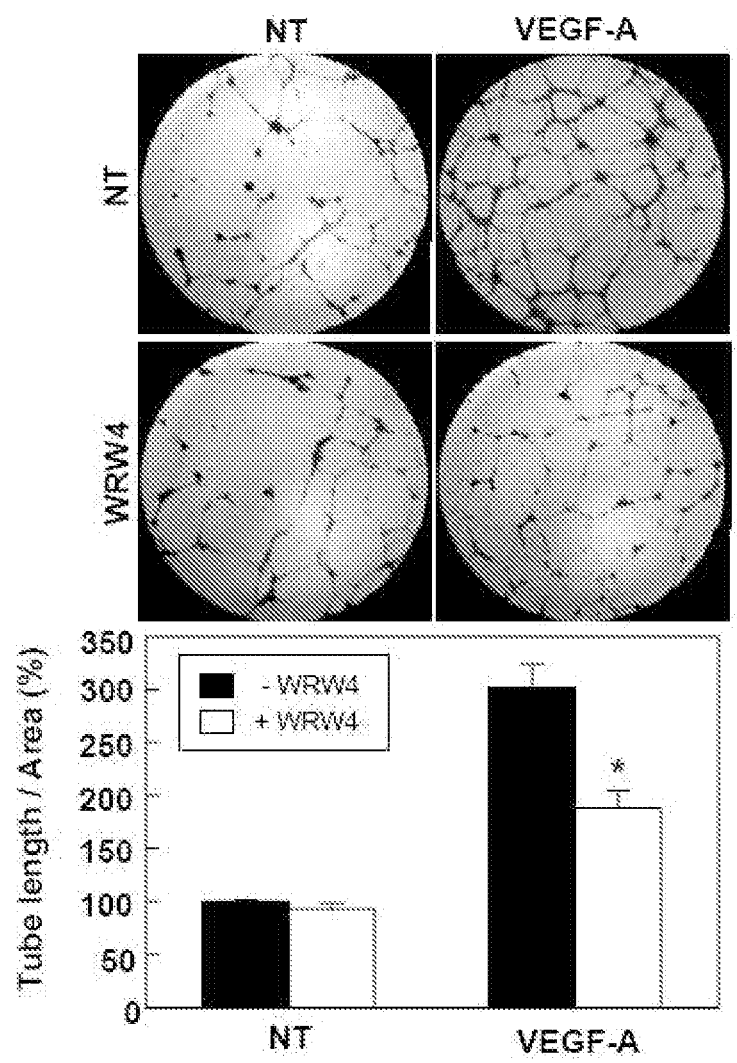
FIG. 24 shows the experiment result confirming that the tube formation of HUVECs induced by VEGF-A is significantly decreased by FPRL1 antagonist (WRW4).

First, 20 ng/ml of VEGF-A was administered to HUVECs, the degree of cell proliferation, cell migration, or tube formation was confirmed by the <Experiment method 9>, and the results are shown in FIGS. 22 to 24. At this time, FPRL1 antagonist WRW4 was additionally added.

As shown in FIG. 22, it can be seen that VEGF-A induces proliferation of HUVECs, but FPRL1 antagonist WRW4 did not exhibit statistically significant inhibition of HUVECs proliferation by VEGF-A.

And, as shown in FIG. 23, it can be seen that VEGF-A induces migration of HUVECs, and in case the cells are treated with FPRL1 antagonist WRW4 (10 uM), the cell migration is not induced.

And, as shown in FIG. 24, it can be seen that VEGF-A induces tube formation of HUVECs, and in case the cells are treated with FPRL1 antagonist WRW4 (10 uM), the tube formation is not induced.

Figure 25:
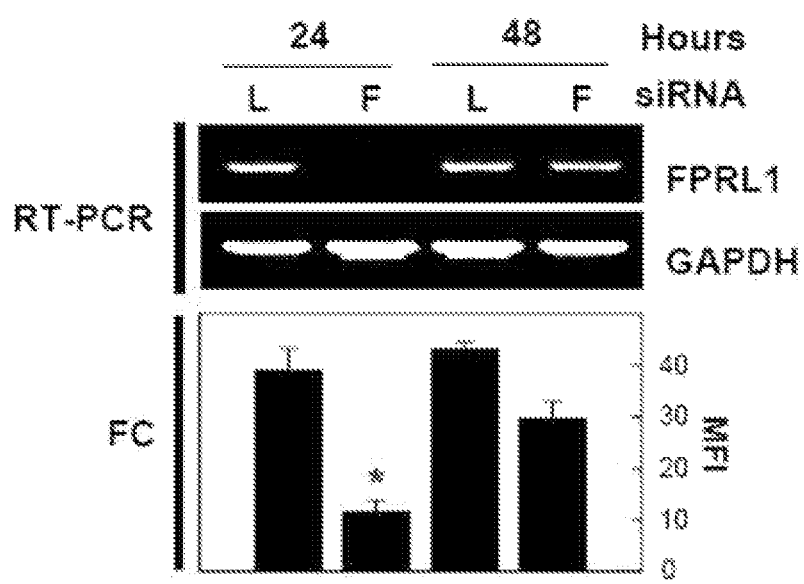
FIG. 25 shows the result confirming that if HUVECs is treated with FPRL1 siRNA, FPRL1 expression is inhibited.

Meanwhile, as described in the <Experiment method 11>, FPRL1 expression was inhibited using FPRL1 siRNA, and RT-PCR was conducted according to the <Experiment method 12> to measure the degree of FPRL1 expression, and the results are shown in FIG. 25.

As shown in FIG. 25, it can be seen that when HUVECs are treated with FPRL1 siRNA, FPRL1 expression is inhibited, and in case treated with Luciferase siRNA as control, FPRL1 expression is not inhibited.

Figure 26:
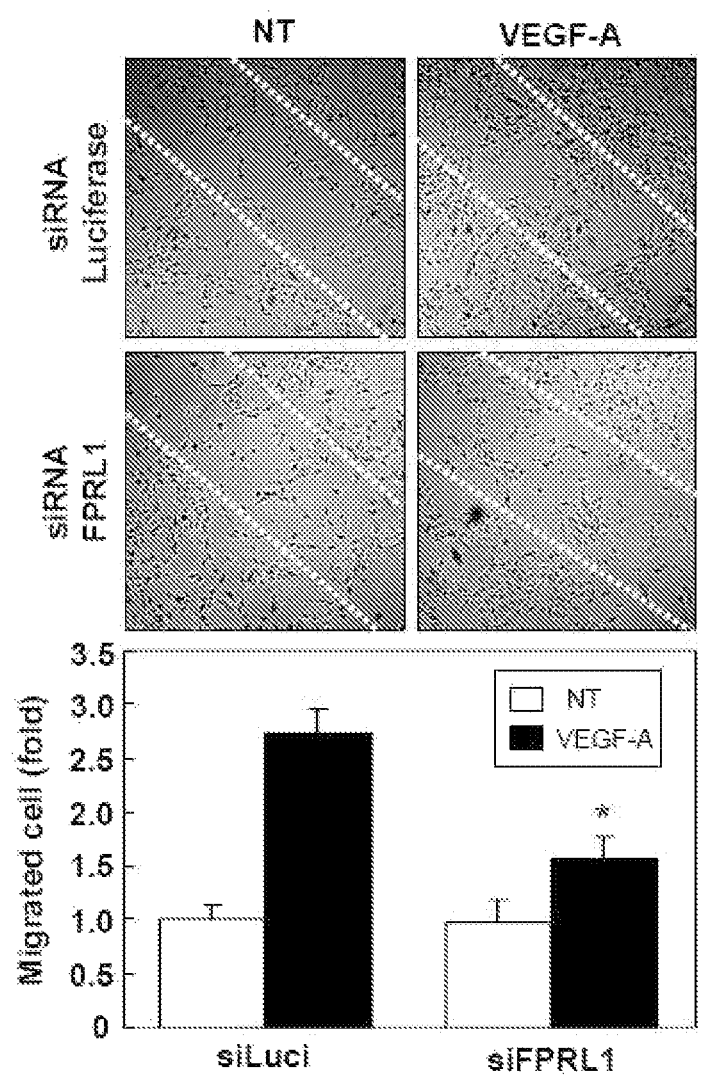
FIG. 26 shows the result confirming that if HUVECs is treated with FPRL1 siRNA, cell migration induced by VEGF-A is inhibited.
Figure 27:
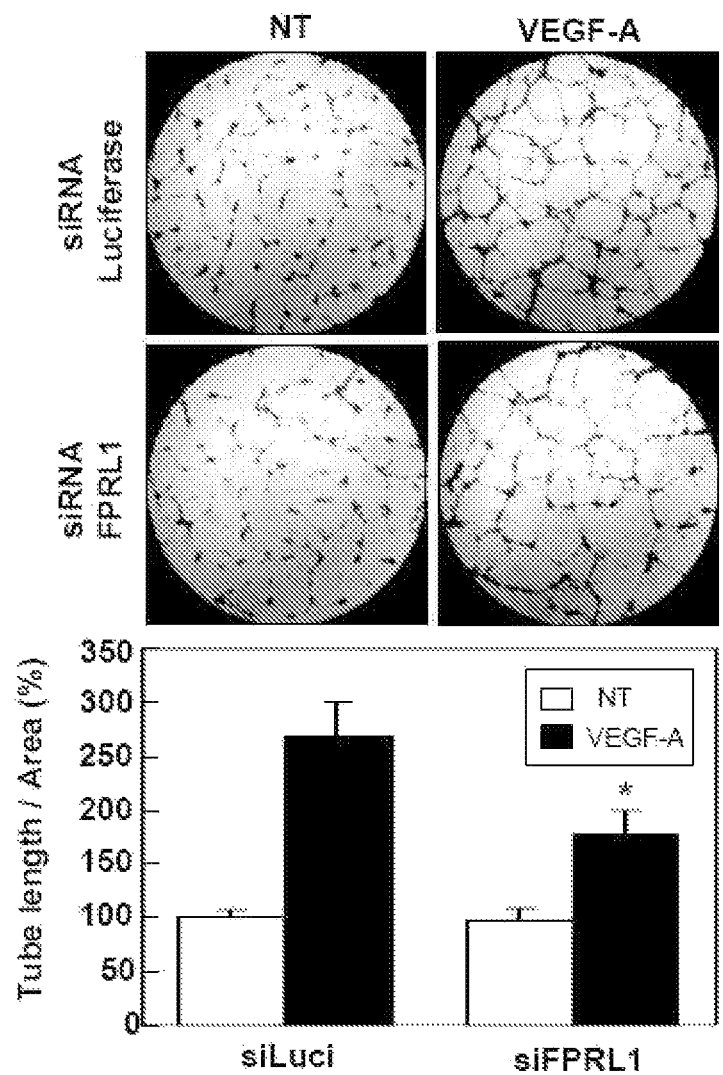
FIG. 27 shows the result confirming that if HUVECs is treated with FPRL1 siRNA, tube formation induced by VEGF-A is inhibited.

Thus, it was confirmed that in case HUVECs are treated with FPRL1 siRNA, cell migration or tube formation induced by VEGF-A is inhibited, and the results are shown in FIGS. 26 and 27.

As shown in FIGS. 26 and 27, in case HUVECs are treated with FPRL1 siRNA, cell migration or tube formation induced by VEGF-A is inhibited compared to the case where HUVECs are treated with Luciferase siRNA as control.

Figure 28:
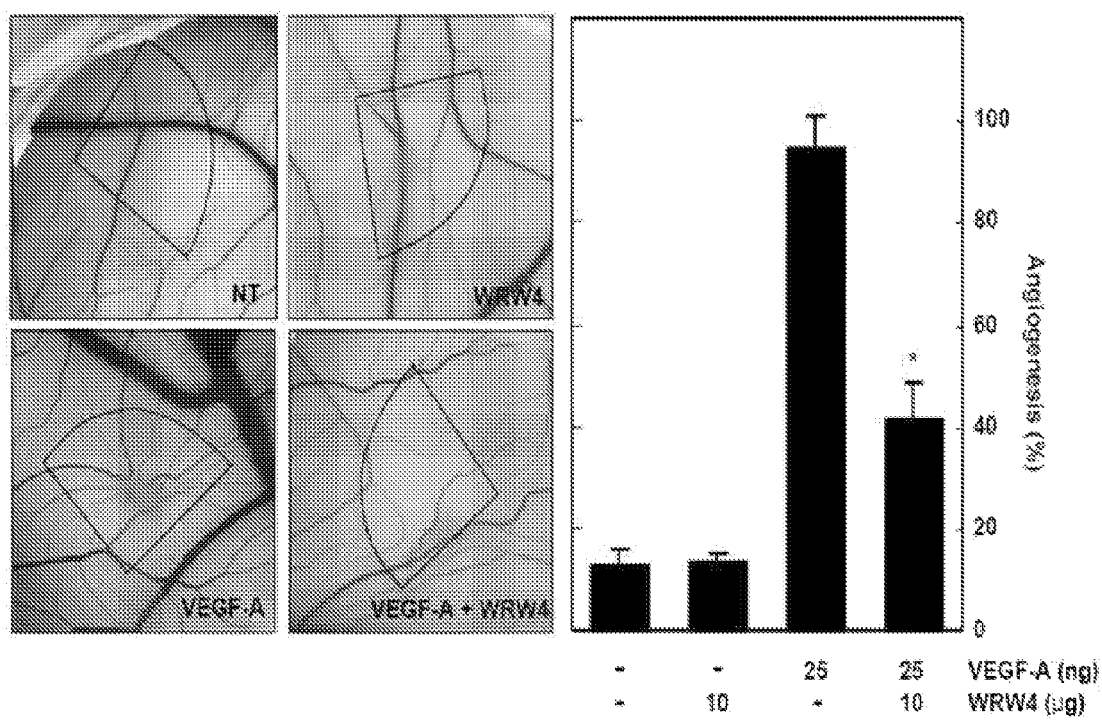
FIG. 28 shows the result confirming that FPRL1 antagonist (WRW4) inhibits angiogenesis by VEGF-A.
Figure 29:
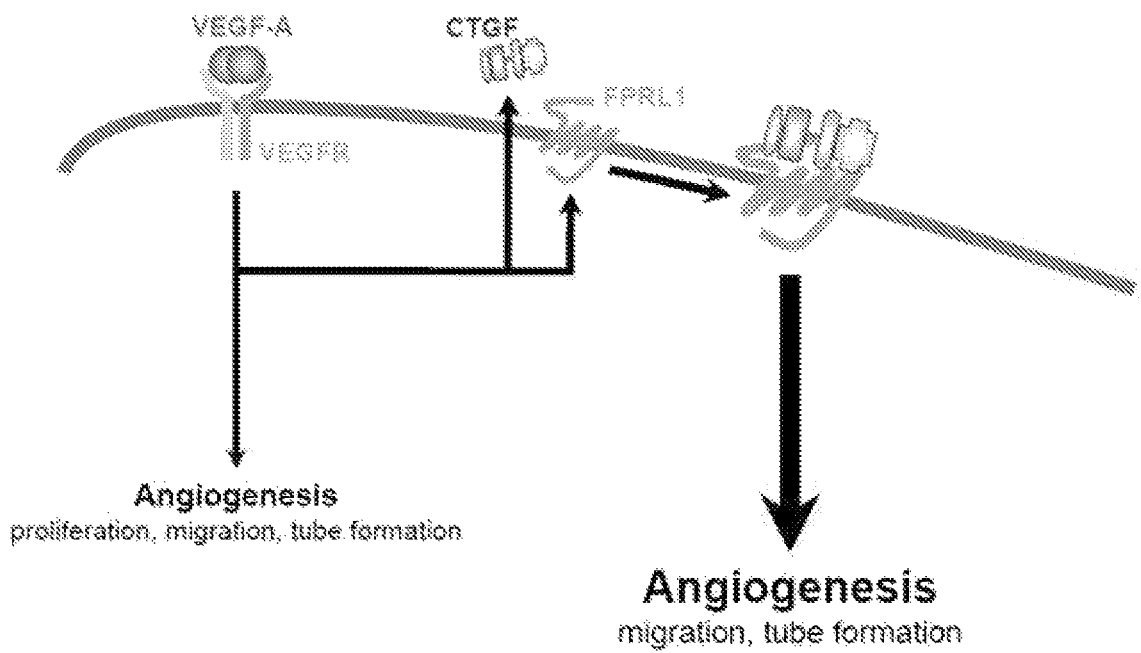
FIG. 29 is a schematic diagram showing the mechanism of angiogenesis that is induced by binding of CTGF expressed by VEGF-A and FPRL1.

And, it was confirmed by the <Experiment method 10> that in case HUVECs are treated with FPRL1 antagonist (10 ug/CAM) in vivo, angiogenesis activity of VEGF-A (25 ng/CAM) is inhibited, and the results are shown in FIG. 28.

As shown in FIG. 28, it can be seen that FPRL1 antagonist strongly inhibits angiogenesis induced by VEGF-A.

From the results, it can be seen that FPRL1 is an important factor for angiogenesis induced by VEGF-A, and that CTGF is an important factor for inducing activation of FPRL1. Namely, it can be seen that FPRL1 and CTGF induced by VEGF-A promote migration of endothelial cells and tube formation by binding therebetween, thus involved in angiogenesis induced by VEGF-A.

The invention claimed is:

1. A method for promoting angiogenesis, the method comprising administering a fragment of connective tissue growth factor protein consisting of the amino acid sequence of SEQ ID NO. 5 or the amino acid sequence of SEQ ID NO. 6 to a patient in need of promoting angiogenesis.

* * * * *